US011401306B2

(12) United States Patent
Bedu-Addo et al.

(10) Patent No.: US 11,401,306 B2
(45) Date of Patent: Aug. 2, 2022

(54) HPV16 NON HLA-RESTRICTED T-CELL VACCINES, COMPOSITIONS AND METHODS OF USE THEREOF

(71) Applicant: PDS Biotechnology Corporation, North Brunswick, NJ (US)

(72) Inventors: Frank Bedu-Addo, Stamford, CT (US); Greg Conn, Madrid (ES); Martin Ward, Lexington, KY (US); Jerold Woodward, Lexington, KY (US)

(73) Assignee: PDS Biotechnology Corporation, North Brunswick, NJ (US)

( * ) Notice: Subject to any disclaimer, the term of this patent is extended or adjusted under 35 U.S.C. 154(b) by 0 days.

(21) Appl. No.: 15/724,818

(22) Filed: Oct. 4, 2017

(65) Prior Publication Data

US 2018/0094032 A1 Apr. 5, 2018

Related U.S. Application Data

(60) Provisional application No. 62/404,458, filed on Oct. 5, 2016.

(51) Int. Cl.
| | |
|---|---|
| *C07K 14/025* | (2006.01) |
| *C07K 14/01* | (2006.01) |
| *A61K 9/127* | (2006.01) |
| *A61K 39/12* | (2006.01) |
| *C07K 14/005* | (2006.01) |
| *A61K 9/00* | (2006.01) |
| *A61K 39/00* | (2006.01) |

(52) U.S. Cl.
CPC .......... *C07K 14/005* (2013.01); *A61K 9/0019* (2013.01); *A61K 9/1272* (2013.01); *A61K 39/12* (2013.01); *A61K 2039/55555* (2013.01); *A61K 2039/585* (2013.01); *C12N 2710/20022* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | | | |
|---|---|---|---|---|
| 7,488,791 B2 * | 2/2009 | Maillere | ............... | A61K 39/12 530/300 |
| 10,155,049 B2 | 12/2018 | Bonnet et al. | | |
| 2004/0203051 A1 | 10/2004 | Simard et al. | | |
| 2010/0203080 A1 * | 8/2010 | Maillere | ............... | C07K 14/005 424/202.1 |
| 2013/0243723 A1 | 9/2013 | Hadden et al. | | |
| 2015/0110823 A1 * | 4/2015 | Bedu-Addo | ....... | A61K 39/0011 424/186.1 |
| 2015/0250872 A1 | 9/2015 | Bedu-Addo et al. | | |
| 2015/0283219 A1 | 10/2015 | Langlade Demoyen et al. | | |
| 2016/0193316 A1 | 7/2016 | Sette et al. | | |
| 2016/0251406 A1 | 9/2016 | Schlom et al. | | |

FOREIGN PATENT DOCUMENTS

| | | |
|---|---|---|
| JP | 2010-537961 A | 12/2010 |
| WO | 01/019408 A1 | 3/2001 |
| WO | 2007/121895 A2 | 11/2007 |
| WO | 2013/188627 A2 | 12/2013 |
| WO | 2016/146618 A1 | 9/2016 |

OTHER PUBLICATIONS

Vasievich et al. Enantiospecific adjuvant activity of cationic lipid DOTAP in cancer vaccine. Cancer Immunol Immunother (2011) 60: 629-638.*
Tsang et al. Identification and characterization of enhancer agonist human cytotoxic T-cell epitopes of the human papillomavirus type 16 (HPV16) E6/E7. Vaccine 35 (2017) 2605-2611.*
Kenter et al. Vaccination against HPV-16 Oncoproteins for Vulvar Intraepithelial Neoplasia. N Engl J Med 2009; 361:1838-47.*
Varypataki et al. Cationic Liposomes Loaded with a Synthetic Long Peptide and Poly(I:C): a Defined Adjuvanted Vaccine for Induction of Antigen-Specific T Cell Cytotoxicity. The AAPS Journal, Jan. 2015; 17(1): 216-226.*
Welters et al. Induction of Tumor-Specific CD4+ and CD8+ T-Cell Immunity in Cervical Cancer Patients by a Human Papillomavirus Type 16 E6 and E7 Long PeptidesVaccine. Clin Cancer Res 2008; 14(1): 178-187.*
De Oliveira et al. et al. Design of Immune Responses and Anti-Tumor Potential of an HPV16 E6E7 Multi-Epitope Vaccine . PLoS ONE 10(9): e0138686.*
Riemer, Angelika B. et al., "A Conserved E7-derived Cytotoxic T Lymphocyte Epitope Expressed on Human Papillomavirus 16-transformed HLA-A2 EEithelial Cancers", *Journal of Biological Chemistry*, vol. 285, No. 38, Sep. 17, 2010, pp. 29608-29622.
Hassan, Chopie et al., "Naturally Processed Non-canonical HLA-A*02:01 Presented Peptides", *Journal of Biological Chemistry*, vol. 290, No. 5, Jan. 30, 2015, pp. 2593-2603.
Yao, Yufeng et al., "HPV-16 E6 and E7 protein T cell epitopes prediction analysis based on distributions of HLA-A loci across populations An in silico approach", *Vaccine*, vol. 31, No. 18, 2013, pp. 2289-2294.
Xiao, Xue et al., "HLA-A, HLA-B, HLA-DRB1 Polymorphisms and Risk of Cervical Squamous Epithelial Cell Carcinoma: A Population Study in China", *Asian Pacific Journal of Cancer Prevention*, vol. 14, No. 7, 2013, pp. 4427-4133.

(Continued)

*Primary Examiner* — Nianxiang Zou
(74) *Attorney, Agent, or Firm* — DLA Piper LLP (US)

(57) ABSTRACT

Novel human papillomovirus immunogenic compositions and methods of use thereof are provided. The compositions comprise unique combinations of multi-epitope peptide sequences specifically selected and designed to be effectively processed and cross-presented to T-cells. The peptides utilized in the compositions display high levels of binding with HLA-supertypes. The immunogenic compositions are broadly applicable to large proportions of target populations. The compositions comprise adjuvants such as cationic lipids.

10 Claims, 3 Drawing Sheets

Specification includes a Sequence Listing.

(56) References Cited

OTHER PUBLICATIONS

Grabowska, Agnieszka K. et al., "Identification of promiscuous HPV16-derived T helper cell epitopes for therapeutic HPV vaccine design", *Int. J. Cancer*, vol. 136, No. 1, 2015, pp. 212-224.
International Search Report and Written Opinion from corresponding International Application No. PCT/US2017/055119; dated Mar. 7, 2018.
International Preliminary Report on Patentability from counterpart International Application No. PCT/US2017/055119, dated Apr. 18, 2019.
Extended European Search Report from counterpart European Application No. 17859111.1 dated May 26, 2020.
Examination Report No. 2 from corresponding Australian Patent Appln. No. 2017340407 dated Jan. 6, 2021.
The Notice of Reasons for Rejection dated Oct. 26, 2021, of counterpart Japanese Patent Application No. 2019-518245, along with an English translation.

* cited by examiner

HPV16 NON HLA-RESTRICTED T-CELL VACCINES, COMPOSITIONS AND METHODS OF USE THEREOF

TECHNICAL FIELD

Embodiments of the present disclosure relate generally to novel HPV16 vaccines, in particular, non HLA-restricted T-cell vaccines, compositions and methods of use thereof.

BACKGROUND

Therapeutic vaccination with HPV E6 and E7 protein antigens has been demonstrated to provide strong potential to treat HPV-induced cancers such as cervical, anal, vulvar, vaginal and head and neck cancers as well as the pre-cancerous neoplasias. Due to limited ability to perform antigen-cross presentation to induce HPV-specific T-cell responses, the earliest approaches to HPV therapeutic vaccination depended on the inclusion and presentation of short single CD8+ peptide epitopes. These peptide-based HPV vaccines due to the restricted HLA-A2 epitopes demonstrated very limited applicability even within the selected HLA-A2 populations evaluated. More recent approaches to overcome this critical drawback of cancer vaccines have focused on 2 key approaches or platforms: 1. The delivery of HPV full-length protein DNA encoded into live vectors such as modified viruses and bacteria. 2. The use of multiple overlapping long multi-epitope peptides covering the entire full length HPV16 E6 and E7 proteins sequences. Both approaches are geared towards overcoming patient genetic restrictions faced using short single-epitope HLA-A2 peptides in order to address a broad patient population, and both approaches show potential promise in human clinical trials.

In-silico peptide binding analysis has been used effectively to understand the potential binding capacity of immunogenic peptides. This technique however has not been used to more efficiently design cancer vaccines which have the characteristics of being simple and yet still have the potential to address the needs of broad patient populations with varied genetic backgrounds.

T cells mediate a range of immune responses, including those responsible for the clearance of intracellular pathogens, virus-infected cells and tumor cells, as well as those responsible for transplant rejection and autoimmunity. The T cell immune system is adapted to recognize foreign cells as well as altered self-cells and eliminate them from the body. T cell recognition of peptide antigens occurs via the T cell receptor (TCR). The process requires that the peptide antigen be presented to the TCR by a major histocompatibility complex (MHC) molecule located on the surface of an antigen presenting cell (APC) such as a dendritic cell. The Human MHC molecules are referred to as human histocompatibility leukocyte antigens (HLA). The peptide antigen is attached to the MHC molecule in a manner that enables the T cell receptor to recognize the unique structure formed by the combination of the MHC molecule and the specific peptide. A limiting aspect of T cell functionality is that polymorphisms in the MHC molecules, as well as the wide spectrum of unique peptides that can associate with the MHC, result in a diverse recognition pattern such that a given MHC-peptide combination is only recognized by a fraction of T cell clones.

There are two major types of MHC molecules involved in antigen presentation: class I and class II. MHC class I molecules are composed of an alpha chain with 3 domains as well as transmembrane and cytoplasmic domains. MHC class I molecules are widely distributed and are present on all nucleated cells. MHC class II molecules are composed of an alpha chain and a beta chain that self-associate to form a heterodimer. Each chain has two extracellular domains, as well as transmembrane and intracellular domains. MHC class II molecules are more restricted in distribution than are class I molecules and are present, for example, on antigen presenting cells (APCs).

Cytotoxic T lymphocytes ("CTL") which have been specifically activated against a particular antigen are capable of killing the cell that contains or expresses the antigen. The TCR of a CTL recognizes an antigen in the context of a MHC class I molecule. An important role for T helper lymphocytes ("Th cells") is the optimal induction of a CTL response and they may also play a role in maintenance of CTL memory. The TCR of a Th cell recognizes an antigen in the context of a MHC class II molecule.

Therapeutic vaccination to prime antigen-recognizing T-cells has been demonstrated to be a viable option for active immunotherapy of cancers that aim to treat both early and late stage disease by activating a patient's immune system. The various mechanisms activated by therapeutic vaccination specifically attack and destroy antigen-expressing cancer cells and ignore normal cells. Therapeutic cancer vaccines, in principle, may therefore be effective at inhibiting tumor growth as well as treating recurrent tumors that are refractory to conventional therapies, such as surgery, radiation and chemotherapy. A therapeutic cancer vaccine to treat prostate cancer has already been approved by the U.S. Food and Drug Administration. This major breakthrough has paved the way for novel approaches to therapeutic vaccination that may provide improved safety and efficacy. Several such approaches are currently being evaluated both pre-clinically and clinically. Unlike prophylactic antibody-inducing vaccines that are generally administered to healthy individuals, therapeutic cancer vaccines are administered to cancer patients and designed to eradicate cancer cells through strengthening patient's own immune responses, specifically T-cell responses (Lollini P L, Cavallo F, Nanni P, Forni G. *Vaccines for tumour prevention. Nature reviews. Cancer.* 2006; 6:204-216).

Tumor-Associated Antigens as Therapeutic Targets

Recombinant vaccines, which are based on proteins from defined tumor-associated antigens (TAAs), or synthetic peptide vaccines derived from TAAs, usually administered in combination with an adjuvant or an immune modulator, present significant advantages in cost and simplicity over autologous and DC vaccines. The availability of patient's samples or specimens and the complex procedure of preparing the individualized vaccines limit the broad use of autologous cancer vaccines. MAGE-1 is the first gene reported to encode a human tumor antigen recognized by T cells (van der Bruggen P, Traversari C, Chomez P, Lurquin C, De Plaen E, Van den Eynde B, Knuth A, Boon T. *A gene encoding an antigen recognized by cytolytic T lymphocytes on a human melanoma. Science.* 1991; 254:1643-1647, and has been well studied and used in clinical cancer vaccines. The identification of several TAAs has provided the ability to develop and design various targeted therapeutic vaccines to address a broad range of cancers. Such TAAs have been classified into several major categories. Cancer-testis antigens, such as NY-ESO-1, BAGE, MAGE, and SSX-2, are encoded by genes that are typically silenced in adult tissues but transcriptionally reactivated in tumor cells (De Smet C, Lurquin C, van der Bruggen P, De Plaen E, Brasseur F, Boon T. *Sequence and expression pattern of the human MAGE2 gene. Immunogenetics.* 1994; 39:121-129; Gnjatic S, Ritter E, Buchler M W, Giese N A, Brors B, Frei C, Murray A, Halama N, Zomig I, Chen Y T, Andrews C, Ritter G, Old L J, Odunsi K, Jager D. *Seromic profiling of ovarian and pancreatic cancer. Proceedings of the National Academy of Sciences of the United States of America.* 2010; 107:5088-5093; Hofmann O, Caballero O L, Stevenson B J, Chen Y T, Cohen T, Chua R, Maher C A, Panji S, Schaefer U, Kruger A, Lehvaslaiho M, Carninci P, Hayashizaki Y, Jongeneel C V, Simpson A J, Old L J, Hide W. *Genome-wide analysis of cancer/testis gene expression. Proceedings of the National Academy of Sciences of the United States of America.* 2008; 105:20422-20427; Karbach J, Neumann A, Atmaca A, Wahle C, Brand K, von Boehmer L, Knuth A, Bender A, Ritter G, Old L J, Jager E. *Efficient in vivo priming by vaccination with recombinant NY-ESO-1 protein and CpG in antigen naive prostate cancer patients. Clinical cancer research: an official journal of the American Association for Cancer Research.* 2011; 17:861-870). The tissue differentiation antigens are antigens of normal tissue origin and shared by both normal tissue and tumors, but elevated in tumor cells, such as melanoma (gp100, Melan-A/Mart-1 and tyrosinase) (Bakker A B, Schreurs M W, de Boer A J, Kawakami Y, Rosenberg S A, Adema G J, Figdor C G. *Melanocyte lineage-specific antigen gp100 is recognized by melanoma-derived tumor-infiltrating lymphocytes. J Exp Med.* 1994; 179:1005-1009. Bakker A B, Schreurs M W, de Boer A J, Kawakami Y, Rosenberg S A, Adema G J, Figdor C G. *Melanocyte lineage-specific antigen gp100 is recognized by melanoma-derived tumor-infiltrating lymphocytes. J Exp Med.* 1994; 179:1005-1009), prostate cancer (PSA, PAP) (Correale P, Walmsley K, Nieroda C, Zaremba S, Zhu M, Schlom J, Tsang K Y. *In vitro generation of human cytotoxic T lymphocytes specific for peptides derived from prostate-specific antigen. J Natl Cancer Inst.* 1997; 89:293-300; Kantoff P W, Higano C S, Shore N D, Berger E R, Small E J, Penson D F, Redfern C H, Ferrari A C, Dreicer R, Sims R B, Xu Y, Frohlich M W, Schellhammer P F. *Sipuleucel-T immunotherapy for castration-resistant prostate cancer. The New England journal of medicine.* 2010a; 363:411-422) and breast carcinomas (mammaglobin-A) (Jaramillo A, Majumder K, Manna P P, Fleming T P, Doherty G, Dipersio J F, Mohanakumar T. *Identification of HLA-A3-restricted CD8+ T cell epitopes derived from mammaglobin-A, a tumor-associated antigen of human breast cancer. International journal of cancer. Journal international du cancer.* 2002; 102:499-506). Similar to these differentiation-associated antigens, several other tumor antigens, such as CEA (Tsang K Y, Zaremba S, Nieroda C A, Zhu M Z, Hamilton J M, Schlom J. *Generation of human cytotoxic T cells specific for human carcinoembryonic antigen epitopes from patients immunized with recombinant vaccinia-CEA vaccine. J Natl Cancer Inst.* 1995; 87:982-990), MUC-1 (Finn O J, Gantt K R, Lepisto A J, Pejawar-Gaddy S, Xue J, Beatty P L. *Importance of MUC1 and spontaneous mouse tumor models for understanding the immunobiology of human adenocarcinomas. Immunologic research.* 2011; 50:261-268), HER2/Neu (Disis M L, Wallace D R, Gooley T A, Dang Y, Slota M, Lu H, Coveler A L, Childs J S, Higgins D M, Fintak P A, dela Rosa C, Tietje K, Link J, Waisman J, Salazar L G. *Concurrent trastuzumab and HER2/neu-specific vaccination in patients with metastatic breast cancer. Journal of clinical oncology, official journal of the American Society of Clinical Oncology.* 2009; 27:4685-4692), tumor suppressor genes (p53) (Azuma K, Shichijo S, Maeda Y, Nakatsura T, Nonaka Y, Fujii T, Koike K, Itoh K. *Mutated p53 gene encodes a nonmutated epitope recognized by HLA-B*4601-restricted and tumor cell-reactive CTLs at tumor site. Cancer Res.* 2003; 63:854-858), hTERT (Vonderheide R H, Hahn W C, Schultze J L, Nadler L M. *The telomerase catalytic subunit is a widely expressed tumor-associated antigen recognized by cytotoxic T lymphocytes. Immunity.* 1999; 10:673-679) and certain anti-apoptotic proteins (e.g. survivin) (Vonderheide R H, Hahn W C, Schultze J L, Nadler L M. *The telomerase catalytic subunit is a widely expressed tumor-associated antigen recognized by cytotoxic T lymphocytes. Immunity.* 1999; 10:673-679) are also highly elevated in tumor tissues compared to normal counterparts. Unique tumor-specific antigens are often referred to mutated oncogenes (ras, B-raf) (Brichard V G, Lejeune D. *Cancer immunotherapy targeting tumour-specific antigens: towards a new therapy for minimal residual disease. Expert opinion on biological therapy.* 2008; 8:951-968). Targeting these tumor-specific antigens involved in driving the neoplastic process has the advantage of resistance to immunoselection with potential to be more effective. While numerous such tumor-specific antigens have been identified and utilized, there continues to be a growing demand for the identification of additional such antigens for a variety of reasons: given the wide variety of genetic profiles among the human population, there is need to identify antigens with increasing specificity for particular groups regardless of how such groups are identified, be it ethnicity or geographic location, for example. There continues to be a need in the pharmaceutical industry to make the process of vaccine production more accurate and less cumbersome, and accordingly isolating antigens, proteins and peptides most precisely associated with eliciting an appropriate immunological response is an ongoing goal.

Protein/peptide-based vaccines have a clear cost advantage over autologous or individualized vaccines. However, the fact that they target only one epitope or a few epitopes of the TAA may be considered a disadvantage. It is generally believed that induction of both antigen-specific CTLs and antigen-specific CD4+ helper T cells is necessary for a cancer vaccine to be optimally efficacious. Some polypeptide vaccines (e.g., Stimuvax®) potentially contain both CD4 and CD8 epitopes. Another approach to enhancing immunogenicity of a self-antigen has been to alter the peptide sequence of TAAs to introduce enhancer agonist epitopes, which increase peptide binding to the MHC molecule or the T-cell receptor, resulting in higher levels of T-cell responses and/or higher avidity T cells (Dzutsev A H, Belyakov I M, Isakov D V, Margulies D H, Berzofsky J A. *Avidity of CD8 T cells sharpens immunodominance. International immunology.* 2007; 19:497-507; Jordan K R, McMahan R H, Kemmler C B, Kappler J W, Slansky J E. *Peptide vaccines prevent tumor growth by activating T cells that respond to native tumor antigens. Proceedings of the National Academy of Sciences of the United States of America.* 2010; 107:4652-4657; Rosenberg S A, Yang J C, Schwartzentruber D J, Hwu P, Marincola F M, Topalian S L, Restifo N P, Dudley M E, Schwarz S L, Spiess P J, Wunderlich J R, Parkhurst M R, Kawakami Y, Seipp C A, Einhorn J H, White D E. *Immunologic and therapeutic evaluation of a synthetic peptide vaccine for the treatment of patients with metastatic melanoma. Nat Med.* 1998; 4:321-327).

A common approach to therapeutic cancer vaccination has been vaccination with exact MHC human leukocyte antigen (HLA) binding peptide derived from the sequence of TAA. T cells recognize their target antigens as peptides of 8-10 amino acids presented by MHC class I molecules at the cell surface. A major drawback to such an approach is the fact that humans are genetically diverse with a broad range of HLA alleles that recognize and bind different peptide antigens. As a result, cancer vaccines based on short peptides have demonstrated very limited applicability and recent approaches have required the inclusion of several peptides sometimes over 10 peptides in order to provide reasonable coverage of the population.

HPV Vaccines

HPV E6 and E7 proteins are constitutively co-expressed in all HPV infected precancerous cells and are the most abundant viral transcripts found in biopsies from HPV-related cervical carcinoma cells (K. Seedorf, T. Oltersdorf, G. Krämmer, W. Röwekamp, Identification of early proteins of the human papilloma viruses type 16 (HPV 16) and type 18 (HPV 18) in cervical carcinoma cells. EMBO J. 6, 139-144 (1987).) Because of their interaction with the p53 and retinoblastoma proteins (D. Pim, A. Storey, M. Thomas, P. Massimi, L. Banks, *Mutational analysis of HPV-18 E6 identifies domains required for p53 degradation in vitro, abolition of p53 transactivation in vivo and immortalisation of primary BMK cells.* Oncogene 9, 1869-1876 (1994)), E6 and E7 are responsible for the transformation of cells and are required for the maintenance of HPV-associated malignancies (K. Münger, P. M. Howley, *Human papillomavirus immortalization and transformation functions.* Virus Res. 89, 213-228 (2002)). Notably, E6- and E7-specific cellular immune responses are associated with regression of HPV16-associated lesions (S. Peng, C. Trimble, L. Wu, D. Pardoll, R. Roden, C. F. Hung, T. C. Wu, *HLA-DQB1*02-restricted HPV-16 E7 peptide-specific CD4+T-cell immune responses correlate with regression of HPV-16-associated high-grade squamous intraepithelial lesions.* Clin. Cancer Res. 13, 2479-2487 (2007)). Farhat et al. reported that, compared to women with persistent cervical HPV16 infection, the percentages of positive enzyme-linked immunospot (ELISpot) responses to HPV16 E6 and E7 are significantly increased among women with recently resolved HPV infection (S. Farhat, M. Nakagawa, A. B. Moscicki, *Cell-mediated immune responses to HPV-16 E6 and E7 antigens as measured by interferon gamma enzyme-linked immunospot in women with cleared or persistent human papillomavirus infection.* Int. J. Gynecol. Cancer 19, 508-512 (2009)). Therefore, the HPV E6 and E7 antigens are considered to be promising immunotherapeutic targets. To date, several types of HPV therapeutic vaccines, including protein/peptide-based vaccines (L. Muderspach, S. Wilczynski, L. Roman, L. Bade, J. Felix, L. A. Small, W. M. Kast, G. Fascio, V. Marty, J. Weber, A phase I trial of a human papillomavirus (HPV) peptide vaccine for women with high-grade cervical and vulvar intraepithelial neoplasia who are HPV 16 positive. Clin. Cancer Res. 6, 3406-3416 (2000); W. J. van Driel, M. E. Ressing, G. G. Kenter, R. M. P. Brandt, E. J. T. Krul, A. B. van Rossum, E. Schuuring, R. OVringa, T. Bauknecht, A. Tamm-Hermelink, P. A. van Dam, G. J. Fleuren, W. M. Kast, C. J. M. Melief and J. B. Trimbos, *Vaccination with HPV16 Peptides of Patients with Advanced Cervical Carcinoma: Clinical Evaluation of a Phase I-II Trial,* Eur J Cancer, Vol. 35, No. 6, pp. 946-952, 1999), have been developed with a focus on stimulating the production and activation of HPV E6 and E7-specific T cells. However, these peptide-based HPV vaccines due to restricted HLA-A2 epitopes demonstrated very limited applicability even within the selected HLA-A2 populations evaluated. It was reported in 2009 that an HPV peptide vaccine containing 13 overlapping peptides from the HPV16 E6 protein and 4 overlapping peptides from the HPV16 E7 peptide, a total of 13 peptides demonstrated robust anti-HPV response when studied in a non-restricted patient population with VIN3. This study provided the first demonstration of a broadly acting HPV peptide vaccine in a non HLA-restricted population (Gemma G. Kenter, Marij J. P. Welters, A. Rob P. M. Valentijn, Margriet J. G. Lowik, Dorien M. A. Berends-van der Meer, Annelies P. G. Vloon, Farah Essahsah, Lorraine M. Fathers, Rienk Offringa, Jan Wouter Drijfhout, Amon R. Wafelman, Jaap Oostendorp, Gert Jan Fleuren, Sjoerd H. van der Burg, and Cornelis J. M. Melief; *Vaccination against HPV-16 Oncoproteins for Vulvar Intraepithelial Neoplasia,* N Engl J Med 2009; 361:1838-47).

These references, particularly the last, by Kenter et al. highlight the major drawbacks associated with the current approach to the development of peptide vaccines that provide broad HLA-coverage. The current approaches, due to their inability to determine the immunogenic sequences that may provide broad coverage, focus on development of long peptides that cover the entire sequence of the antigenic protein. As a result 4 major drawbacks result: 1. the vaccines are complex and contain a large number of peptides e.g. Kenter at al. use 13 peptides; 2. the vaccines are more costly than necessary; 3. patients are subjected to receiving unnecessary peptides that may have no therapeutic or immunogenic benefit whatsoever; and 4. active peptides may be inactivated through competitive binding with other peptides (this particular drawback is reported by Kenter et al cited above).

The current invention reports an efficient approach to the development of simple, more cost effective, and highly effective and broad HLA-covering peptide vaccines.

Immunostimulatory Adjuvants for Protein/Peptide-Based Vaccines

Given that TAAs are poorly immunogenic in nature, an immunostimulatory adjuvant may be necessary in certain cases for generation of an effective immune response. Aluminum salts (alum) have been used as adjuvants with great success for almost a century and have been particularly effective at promoting protective humoral immunity. However, alum is not optimally effective for diseases where cell-mediated immunity is required for protection. The recognition over the past two decades that activation of innate immunity is required to drive adaptive immune responses has radically altered theories as to how adjuvants promote adaptive immunity. In particular, the pioneering work of Charles Janeway demonstrated that adaptive immune responses are preceded by, and dependent on, innate immunity receptors triggered by microbial components (Janeway C A., Jr. *The immune system evolved to discriminate infectious nonself from noninfectious self.* Immunol Today. 1992; 13:11-16). Recognition of conserved moieties associated with pathogen or pathogen-associated molecular patterns (PAMPs) via pattern recognition receptors, e.g., toll-like receptors (TLRs), engages coordinated innate and adaptive immunity against microbial pathogen or infected cells (Kawai T, Akira S. *Toll-like receptors and their crosstalk with other innate receptors in infection and immunity.* Immunity. 2011; 34:637-650). TLR-mediated activation of antigen-presenting cells, e.g., DCs, is a crucial step in this process. Indeed, many established and experimental vaccines incorporate PAMPs, not only to protect against infectious diseases, but also as part of therapeutic immunizations against cancer (Wille-Reece U, Flynn B J, Lore K, Koup R A, Miles A P, Saul A, Kedl R M, Mattapallil J J, Weiss W R, Roederer M, Seder R A. *Toll-like receptor agonists influence the magnitude and quality of memory T cell responses after prime-boost immunization in nonhuman primates.* J. Exp. Med. 2006; 203:1249-1258). The use of these molecularly and functionally defined molecules as adjuvants greatly facilitates the rational design of vaccines.

Supporting this view, long-used BCG (*Bacillus* Calmette-Guerin) for the treatment of bladder carcinoma has been relatively effective and shown to activate TLR2 and TLR4 (Heldwein K A, Liang M D, Andresen T K, Thomas K E, Marty A M, Cuesta N, Vogel S N, Fenton M J. *TLR2 and TLR4 serve distinct roles in the host immune response against Mycobacterium bovis BCG. Journal of leukocyte biology.* 2003; 74:277-286). LPS, a natural ligand of TLR4, was reported to possess anticancer properties as early as the 1960s (Mizuno D, Yoshioka O, Akamatu M, Kataoka T. *Antitumor effect of intracutaneous injection of bacterial lipopolysaccharide. Cancer research.* 1968; 28:1531-1537). Monophosphoryl lipid A (MPL) is a chemically modified derivative of *S. minnesota* endotoxin that exhibits greatly reduced toxicity, but maintains most of the immunostimulatory properties of LPS (Mata-Haro V, Cekic C, Martin M, Chilton P M, Casella C R, Mitchell T C. *The vaccine adjuvant monophosphoryl lipid A as a TRIF-biased agonist of TLR4. Science.* 2007; 316:1628-1632). A plethora of studies have shown that MPL potently boosts a patient's immune response against viral and tumor-associated antigens (Schwarz T F. *Clinical update of the AS04-adjuvanted human papillomavirus-16/18 cervical cancer vaccine, Cervarix. Advances in therapy.* 2009; 26:983-998). FDA approved the Cervarix vaccine formulated with MPL and aluminum salt as a prophylactic vaccine against human papillomavirus (Schiffman M, Wacholder S. *Success of HPV vaccination is now a matter of coverage. The lancet oncology.* 2012; 13:10-12). Imiquimod (a TLR7 agonist) was approved by FDA in 2004 for use in humans against actinic keratosis and superficial basal cell carcinoma (Hoffman E S, Smith R E, Renaud R C., Jr. *From the analyst's couch: TLR-targeted therapeutics. Nat Rev Drug Discov.* 2005; 4:879-880). These TLR agonists have strong potential in promoting the immunogenicity of weakly immunogenic TAAs. Indeed, several peptide/protein-based cancer vaccines combined with TLR agonists are being tested in clinical trials; these include Ampligen targeting TLR3 (NCT01355393), Histonol targeting TLR3 (NCT00773097, NCT01585350, NCT01437605), MELITAC 12.1 targeting TLR4 (NCT01585350) and Resiquimod targeting TLR9 (NCT00960752). The family of PRRs has greatly expanded in recent years, so there is tremendous effort being expended to investigate the role of innate immune pathways in defining the mechanisms of adjuvant action as well as roles of other PRRs (e.g., NLR, RLR) in adjuvant activity of therapeutic cancer vaccines.

In addition to sensing pathogen-associated signals, PRRs also recognize endogenous 'alarmins', such as stress/heat shock proteins (HSPs) and HMGB-1 (Lotze M T, Zeh H J, Rubartelli A, Sparvero L J, Amoscato A A, Washburn N R, Devera M E, Liang X, Tor M, Billiar T. *The grateful dead: damage-associated molecular pattern molecules and reduction/oxidation regulate immunity. Immunol Rev.* 2007; 220:60-81; Todryk S M, Melcher A A, Dalgleish A G, Vile R G. *Heat shock proteins refine the danger theory. Immunology.* 2000; 99:334-337). As intrinsic and highly conserved protein components of the cell, these damage-associated molecular patterns (DAMPs) also communicate the nature and magnitude of cellular injury to the host immune system. Although HSPs are known to act as molecular chaperones that participate in intracellular protein quality control (Calderwood S K, Murshid A, Prince T. *The shock of aging: molecular chaperones and the heat shock response in longevity and aging—a mini-review. Gerontology.* 2009; 55:550-558; Mayer M P, Bukau B. *Hsp70 chaperones: cellular functions and molecular mechanism. Cell Mol Life Sci.* 2005; 62:670-684), studies for the last two decades have established the concept that certain HSPs are capable of integrating both innate and adaptive immune responses, and can be utilized as immunostimulatory agents for cancer immunotherapy (Mayer M P, Bukau B. *Hsp70 chaperones: cellular functions and molecular mechanism. Cell Mol Life Sci.* 2005; 62:670-684; Wang X Y, Facciponte J G, Subjeck J R. *Molecular chaperones and cancer immunotherapy. Handb Exp Pharmacol.* 2006b; 172:305-329).

Though significant strides have been made in the rational design of vaccines, there continues to be an ongoing need for the development of optimized vaccines, both prophylactic and therapeutic. There is a need for the development of vaccines that have broad applicability to large patient populations, and a need for such vaccines to be specific and effective.

SUMMARY

Disclosed herein are novel compositions comprising HPV peptide sequences optionally combined with one or more adjuvants, wherein the HPV peptide sequences correspond to HPV16 E6 peptides, and/or HPV16 E7 peptides and wherein the peptide sequences have a binding affinity of approximately IC50 of 5,000 nM with 5 HLA supertypes, and wherein some of the peptides are multi-epitope peptides. In certain embodiments, the compositions comprise adjuvants consisting of cationic lipids, and in certain embodiments, the cationic lipids consist of DDA, R-DOTAP, DOTAP, DOTMA or DOEPC, variations or analogs thereof. The novel compositions disclosed herein are superior to currently available vaccines in that they are effective for over 80-90% of the general population.

Disclosed herein are methods for inducing an immune response against HPV infection in a subject comprising administering to a subject a composition comprising HPV peptide sequences optionally combined with an adjuvant, wherein the HPV peptide sequences correspond to HPV16 E6 peptides, and/or HPV16 E7 peptides and wherein the peptide sequences have a binding affinity of approximately IC50 of 5,000 nM with 5 HLA supertypes, and wherein some of the peptides are multi-epitope peptides. The methods may be prophylactic or therapeutic.

BRIEF DESCRIPTION OF FIGURES

In FIG. 3, a composition comprising only R-DOTAP is represented by the plot line marked by striped squares.

DETAILED DESCRIPTION

Figure 1:
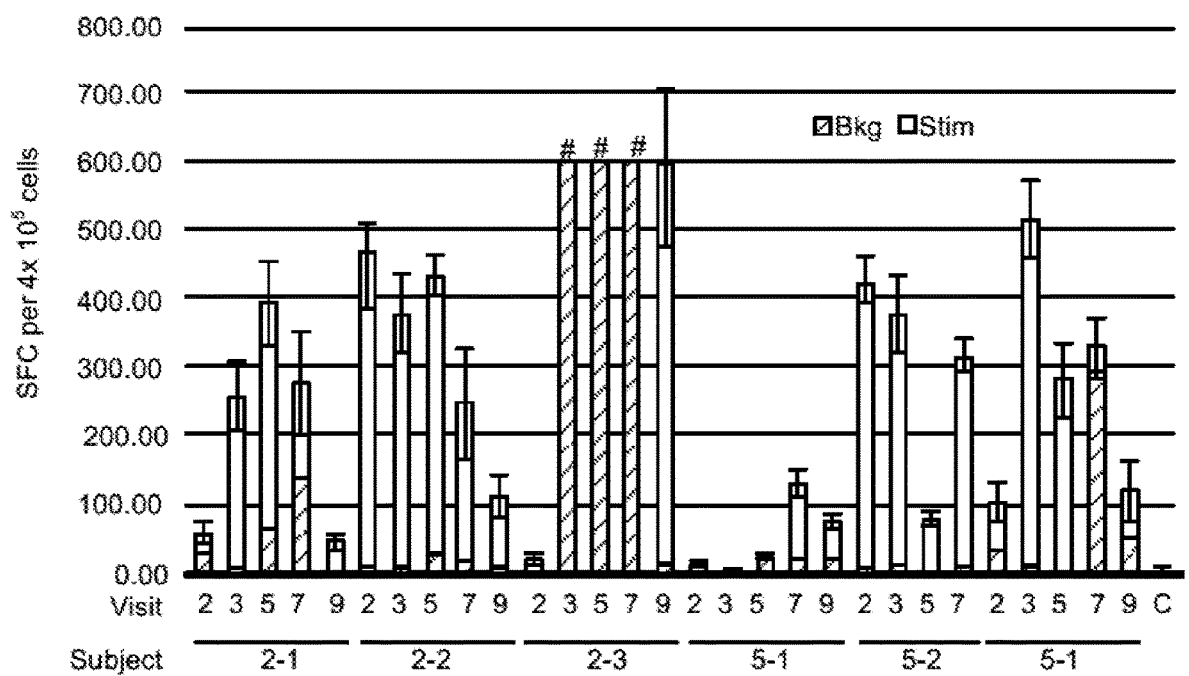
FIG. 1 provides a graph showing anti-HPV-16 E6 and E7 response by interferon-γ assay by subject and visit for 1 mg and 3 mg R-DOTAP Cohorts. Abbreviations: Bkg=background (striped bars); PBMCs=peripheral blood mononuclear cells; R-DOTAP=R-enantiomer of 1,2-dioleoyl-3-trimethylammonium-propane chloride; SFC=SFU=spot-forming units; Stim=stimulated (clear bars). Data represent the mean SFU per $4 \times 10^5$ PBMCs in triplicate wells. Striped bars represent background SFU in wells stimulated with media only. Clear bars represent SFU in wells stimulated with the peptide pool. Visit 2=Day 1 at prevaccination; Visit 3=Day 15, 14 days post Vaccination 1; Visit 5=Day 36, 14 days post Vaccination 2; Visit 7=Day 57, 14 days post Vaccination 3; Visit 9=Day 133, 90 days post Vaccination 3.
Figure 2:
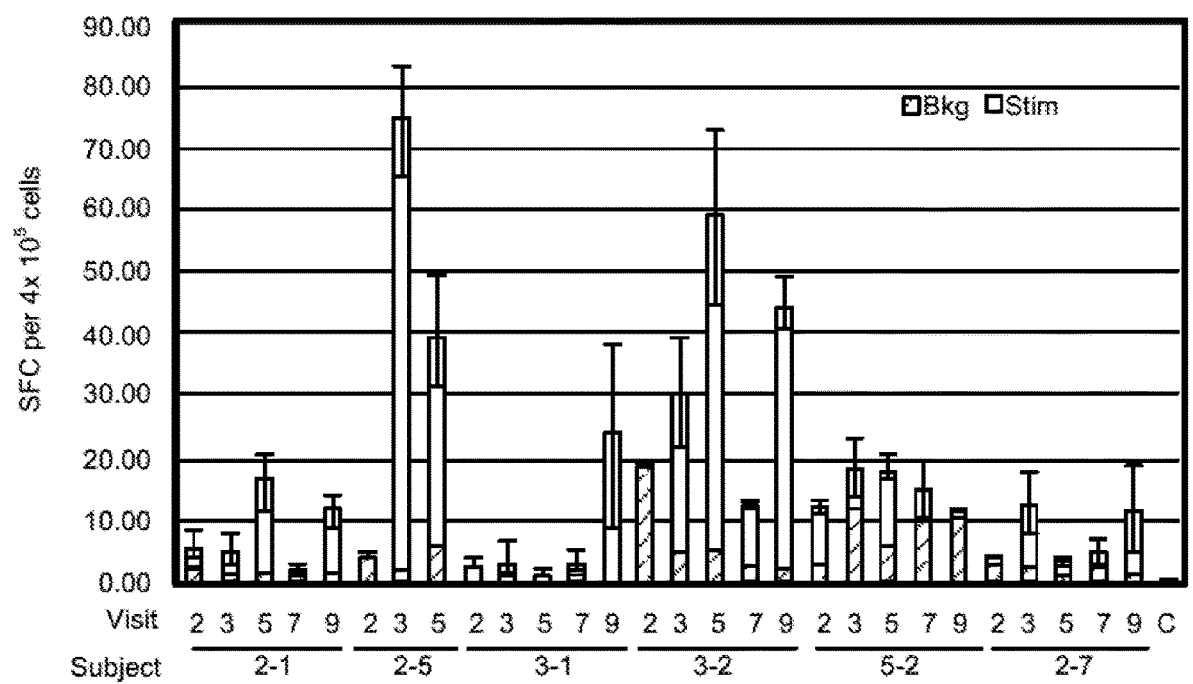
FIG. 2 provides a graph showing anti-HPV-16 E6 and E7 response by interferon-γ assay by subject and visit for the 10 mg R-DOTAP Cohort. The data represent the mean SFU per $4 \times 10^5$ PBMCs in triplicate wells. Striped bars represent background SFU in wells stimulated with media only. Clear bars represent SFU in wells stimulated with the peptide pool. Visit 2=Day 1 at prevaccination; Visit=Day 15, 14 days post Vaccination 1; Visit 5=Day 36, 14 days post Vaccination 2; Visit 7=Day57, 14 days post Vaccination 3; Visit 9=Day 133, 90 days post Vaccination 3.

The following detailed description is exemplary and explanatory and is intended to provide further explanation of the present disclosure described herein. Other advantages, and novel features will be readily apparent to those skilled in the art from the following detailed description of the present disclosure. References mentioned herein, including U.S. Provisional Application Ser. No. 62/404,458, are incorporated by reference in their entirety.

Disclosed herein are methods for the design and use of unique peptide sequences, including unique multi-epitope peptide sequences, derived from HPV16 E6 and E7, designed to be effectively processed and cross-presented to T cells, as screened and demonstrated in HLA-A2 humanized transgenic mice and confirmed in varied human subjects. In certain embodiments, the novel compositions comprising the novel peptide sequences consist of 2-8 peptide sequences, 2-6 peptide sequences, or 4 peptide sequences. The peptides may be incorporated into immunogenic compositions, such as vaccines. As demonstrated below, in-silico peptide binding analysis to the major HLA super types confirms the resulting compositions and vaccines as addressing over 80-90% of the population. In a non HLA-restricted human clinical trial comprising the use of the peptide compositions described herein, strong T-cell induction was confirmed in all subjects. Utilizing the novel approach of in-silico binding analysis combined with testing in humanized transgenic mice, the inventors herein have developed the first simple, effective and broadly applicable peptide-based HPV16 therapeutic cancer vaccines.

An important consideration in the design of peptide-based vaccines designed to elicit CD8+ T cell generation and response in humans, is the polymorphism of the HLA class I molecules in the population. Because different HLA alleles bind different peptides, it is important that a peptide vaccine contain enough different peptides to be immunogenic in a high percentage of the population. The inventors herein designed a novel multi-peptide vaccine to cover immunogenic regions of the HPV16 E6 and E7 proteins to provide correct processing and presentation of CD8+ T-cell epitopes in humans: in an embodiment, the vaccine comprises four HPV-related peptides selected based on their binding and immunogenic activity. As detailed in the Examples, the inventors engaged in ELISpot and tumor regression studies as well as in-silico analysis to predict potential HLA alleles that could bind various HPV peptides. The ability of the human immune system to present and recognize the peptide epitopes was then studied in humanized transgenic mice to confirm presentation, processing and subsequent induction of antigen-specific CD8+ T-cell responses. Finally, the ability to induce human T-cell responses were studied in a non HLA-restricted human clinical trial, and the ability of the formulation to induce strong T-cell responses in subjects with varied HLA sub-types was confirmed.

In an embodiment, the novel compositions as described herein comprise HPV peptide sequences combined with an adjuvant, wherein the HPV peptide sequences correspond to HPV16 E6 peptides, and/or HPV16 E7 peptides and wherein the peptide sequences have a binding affinity of approximately IC50 of 5,000 nM with 5 HLA supertypes, in certain embodiments, the peptides are multi-epitope peptides. The peptides may comprise SEQ ID NOS: 5, 9, 10 and 11, or their lipidated versions comprising SEQ ID NOS: 23, 24, 25 and 26. In an embodiment, the peptides may be present in the composition as individual peptides or they may be conjugated to each other (in any order), either with a spacer or without a spacer, to form a single long peptide encompassing the claimed sequences in accordance with methods known to those skilled in the art. In certain embodiments, the HLA supertypes comprise HLA-A*02:01, HLA-A*03:01, HLA-A*24:02, HLA-B*07:02, and HLA-B*58:01. In some embodiments the compositions may further comprise enhancer agonist epitopes such as the HBV core helper peptide etc., and or single-epitope peptides including, but not limited to peptides encoded by SEQ ID NO: 14, or SEQ ID NO: 15 and analogs thereof such as SEQ ID NOS: 27 and 28. The compositions described herein further comprise modified peptides, peptide analogs, and active fragments thereof. In certain embodiments the peptides may be modified by being oxidized, cross-linked by di-sulfide bonds, pegylated, glycosylated, phosphorylated, palmitoylated, methylated, biotinylated or by other processes known to those skilled in the art to improve efficacy and immunogenicity. In an embodiment, the adjuvant of the composition consists of a cationic lipid, wherein the cationic lipid may be selected from the group consisting of DOTAP, DDA, DOEPC, DOTMA, R-DOTAP, R-DDA, R-DOEPC, R-DOTMA, S-DOTAP, S-DDA, S-DOEPC, S-DOTMA, and variations or analogs thereof. In an embodiment, the novel compositions of the disclosure comprise peptides corresponding to SEQ ID NOS: 5, 9, 10 and 11, the adjuvant comprises a cationic lipid and the cationic lipid comprises R-DOTAP. In an embodiment, the novel compositions of the disclosure comprise peptides corresponding to SEQ ID NOS: 23, 24, 25 or 26, and the adjuvant comprises a cationic lipid wherein the cationic lipid comprises R-DOTAP. In an embodiment, the novel compositions of the disclosure comprise peptides corresponding to SEQ ID NOS: 5, 9, 10, 11, 23, 24, 25 or 26, and the adjuvant comprises a cationic lipid wherein the cationic lipid comprises R-DOTAP. The above described embodiments may be optionally encapsulated in liposomes. The above described embodiments may be optionally combined with a pharmaceutically acceptable carriers and excipients e.g. various buffers such as acetate, phosphate and tonicity adjusters, such as sucrose, trehalose etc., or surfactants such as tween and others known to those skilled in the art.

In an embodiment, the disclosure herein provides recombinant vectors comprising a nucleic acid molecules encoding polypeptides comprising one or more of SEQ ID NO: 5, 9, 10 11, or one or more of SEQ ID NOS: 23, 24, 25 or 26 operably linked to a promoter. Also provided are recombinant vectors comprising nucleic acid molecules encoding polypeptides comprising one or more of SEQ ID NO: 5, 9, 10 11, or one or more of SEQ ID NOS: 23, 24, 25 or 26 operably linked to promoters further comprising nucleic acid molecules encoding enhancer agonist epitopes and/or single-epitope peptides. In an embodiment, the vectors described above may comprise recombinant adenovirus. As is known to those skilled in the art, nucleic acid sequences can be cloned using routine molecular biology techniques, or generated de novo by DNA synthesis, which can be performed using routine procedures by service companies having business in the field of DNA synthesis and/or molecular cloning.

In an embodiment, the disclosure herein provides methods for inducing an immune response against HPV infection in a subject comprising administering to a subject, novel compositions comprising HPV peptide sequences combined with one or more adjuvants, wherein the HPV peptide sequences correspond to HPV16 E6 peptides, and/or HPV16 E7 peptides and wherein the peptide sequences have a binding affinity of approximately IC50 of 5,000 nM with 5 HLA supertypes, and wherein some of the peptides are multi-epitope peptides. The methods disclosed herein for inducing an immune response may include inducing an immune response for prophylactic or therapeutic purposes. In certain embodiments, the peptides used in the novel compositions may comprise one or more peptides selected from the group consisting of SEQ ID NOS: 5, 9, 10 11, 23, 24, 25, 26, 31, 32 or others described herein for example in Tables 1-5. The peptides may be present as individual peptides, or certain selected peptides may be conjugated to each other (in any order) either with a spacer, or without a spacer, to form a single long peptide encompassing the claimed sequences. The methods may comprise use of compositions where the adjuvant consists of a cationic lipid, for example, wherein the cationic lipid comprises DOTAP, DDA, DOEPC, DOTMA, R-DOTAP, R-DDA, R-DOEPC, R-DOTMA, S-DOTAP, S-DDA, S-DOEPC, S-DOTMA, variations or analogs thereof. In an embodiment, the methods for inducing an immune response may comprise administering to a subject a composition comprising the peptides consisting of SEQ ID NOS: 5, 9, 10 11 and R-DOTAP, or a composition the peptides consisting of SEQ ID NOS: 23, 24, 25 or 26 and R-DOTAP.

The methods as described herein, may comprise the use of novel HPV peptide compositions for treating a subject having an HPV infection, wherein the infection comprises symptoms including, but not limited to, common warts, plantar warts, flat warts, genital warts, anogenital warts, anal dysplasia, genital cancers (vulva, vagina, cervix, penis, anus), cancers of the head and neck, epidermaodysplasia verruciformis, focal epithelias hyperplasia, mouth papillomas, oropharyngeal cancer, verrucous cyst, and laryngeal papillomatosis.

It will be appreciated by a skilled person that changes can be made to peptides, e.g., by amino acid substitutions, deletions, additions, etc., e.g., using routine molecular biology procedures. Generally, conservative amino acid substitutions may be applied without loss of function or immunogenicity of a polypeptide. This can be checked according to routine procedures well known to the skilled person.

Also included in the scope of the peptides described herein are modifications of the peptides, and peptide fragments. Such modifications include substitutions of naturally occurring amino acids at specific sites with other molecules, including but not limited to naturally and non-naturally occurring amino acids. Such substitutions may modify the bioactivity of peptides and produce biological or pharmacological agonists or antagonists. Such substitutions may include conservative substitutions known to one of skill in the art, such as valine for alanine. Acceptable substitutions may also include modifications of amino acids, such as norleucine for leucine. It is to be understood that substitution of D amino acids for L amino acids is encompassed within the scope of the present invention. Some substitutions are described in *Dictionary of Biochemistry and Molecular Biology,* 2"a ed., J. Stenesh, John Wiley & Sons, 1989, the entirety of which is incorporated herein by reference. Additional modifications include addition of an amino acid, such as a tyrosine or another amino acid at specific locations in peptides or fragments thereof to enhance labeling potential with radioactive and non-radioactive labels, addition of molecules such as ricin, addition of radioactive and/or nonradioactive labels.

Furthermore, one of skill in the art will recognize that individual substitutions, deletions or additions in the amino acid sequence of disclosed peptides, or in the nucleotide sequence encoding for the amino acids in the peptides, which alter, add or delete a single amino acid or a small percentage of amino acids (typically less than 5%, more typically less than 1%) in an encoded sequence are conservatively modified variations, wherein the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M); Valine (V); and
6) Phenylalanine (F), Tyrosine (Y), Tryptophan (W).

Lipid Adjuvants

Cationic lipids have been reported to have strong immune-stimulatory adjuvant effect. The cationic lipids of the present invention may form liposomes that are optionally mixed with antigen and may contain the cationic lipids alone or in combination with neutral lipids. Suitable cationic lipid species include: 3-β[$^4$N-($^1$N,$^8$-diguanidino spermidine)-carbamoyl] cholesterol (BGSC); 3-β[N,N-diguanidinoethyl-aminoethane)-carbamoyl] cholesterol (BGTC); N,N$^1$N$^2$N$^3$Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2 (sperminecarboxamido)ethyl]-N,N-dimethyl-1-p-ropan-aminium trifluorocetate) (DOSPA); 1,3-dioleoyloxy-2-(6-carboxyspermyl)-propylamide (DOSPER); 4-(2,3-bis-palmitoyloxy-propyl)-1-methyl-1H-imidazole (DPIM) N,N, N',N'-tetramethyl-N,N'-bis(2-hydroxyethyl)-2,3 dioleoyloxy-1,4-butanediammonium iodide) (Tfx-50); N-1-(2,3-dioleoyloxy) propyl-N,N,N-trimethyl ammonium chloride (DOTMA) or other N—(N,N-1-dialkoxy)-alkyl-N,N,N-trisubstituted ammonium surfactants; 1,2 dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-β-hydroxyethylammonium) or DORIE (DL-1,2-O-dioleoyl-3-dimethylaminopropyl-β-hydroxyethylammoniu-m) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycyl-spermine (DOGS) and dipalmitoyl phosphatidylethanolam-ylspermine (DPPES) or the cationic lipids disclosed in U.S.

Pat. No. 5,283,185, cholesteryl-3β-carboxyl-amido-ethylenetrimethylammonium iodide, 1-dimethylamino-3-trimethylammonio-DL-2-propyl-cholesteryl carboxylate iodide, cholesteryl-3-O-carboxyamidoethyleneamine, cholesteryl-3-β-oxysuccinamido-ethylenetrimethylammonium iodide, 1-dimethylamino-3-trimethylammonio-DL-2-propyl-cholesteryl-3-β-oxysuccinateiodide, 2-(2-trimethylammonio)-ethylmethylamino ethyl-cholesteryl-3-β-oxysuccinateiodide, 3-β-N—(N',N'-dimethylaminoethane) carbamoyl cholesterol (DC-chol), and 3-β-N-(polyethyleneimine)-carbamoylcholesterol; O,O'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-distearoyl-sn-glycero-3-ethylphosphocholine (DSEPC); 1,2-dioleoyl-3-trimethylammoninum propane (DOTAP); dioleoyl dimethylaminopropane (DODAP); 1,2-palmitoyl-3-trimethylammonium propane (DPTAP); 1,2-distearoyl-3-trimethylammonium propane (DSTAP), 1,2-myristoyl-3-trimethylammonium propane (DMTAP); and sodium dodecyl sulfate (SDS). The present invention contemplates the use of structural variants and derivatives of the cationic lipids disclosed in this application.

Certain aspects of the present invention include nonsteroidal chiral cationic lipids having a structure represented by the following formula:

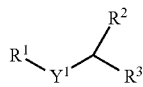

wherein in $R^1$ is a quaternary ammonium group, $Y^1$ is chosen from a hydrocarbon chain, an ester, a ketone, and a peptide, $R^2$ and $R^3$ are independently chosen from a saturated fatty acid, an unsaturated fatty acid, an ester-linked hydrocarbon, phosphor-diesters, and combinations thereof. DOTAP, DMTAP, DSTAP, DPTAP, DPEPC, DSEPC, DMEPC, DLEPC, DOEPC, DMKE, DMKD, DOSPA, DOTMA, are examples of lipids having this general structure.

In one embodiment, chiral cationic lipids of the invention are lipids in which bonds between the lipophilic group and the amino group are stable in aqueous solution. Thus, an attribute of the complexes of the invention is their stability during storage (i.e., their ability to maintain a small diameter and retain biological activity over time following their formation). Such bonds used in the cationic lipids include amide bonds, ester bonds, ether bonds and carbamoyl bonds. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed for certain drug delivery applications [Brunette, E. et al., Nucl. Acids Res., 20:1151 (1992)].

It is to be further understood that in considering chiral cationic liposomes suitable for use in the invention and optionally mixing with antigen, the methods of the invention are not restricted only to the use of the cationic lipids recited above but rather, any lipid composition may be used so long as a cationic liposome is produced and the resulting cationic charge density is sufficient to activate and induce an immune response.

Thus, the lipids of the invention may contain other lipids in addition to the cationic lipids. These lipids include, but are not limited to, lyso lipids of which lysophosphatidylcholine (1-oleoyl lysophosphatidylcholine) is an example, cholesterol, or neutral phospholipids including dioleoyl phosphatidyl ethanolamine (DOPE) or dioleoyl phosphatidylcholine (DOPC) as well as various lipophylic surfactants, containing polyethylene glycol moieties, of which Tween-80 and PEG-PE are examples.

The cationic lipids of the invention may also contain negatively charged lipids as well as cationic lipids so long as the net charge of the complexes formed is positive and/or the surface of the complex is positively charged. Negatively charged lipids of the invention are those comprising at least one lipid species having a net negative charge at or near physiological pH or combinations of these. Suitable negatively charged lipid species include, but are not limited to, CHEMS (cholesteryl hemisuccinate), NGPE (N-glutaryl phosphatidlylethanolanine), phosphatidyl glycerol and phosphatidic acid or a similar phospholipid analog.

Methods for producing the liposomes to be used in the production of the lipid comprising drug delivery complexes of the present invention are known to those of ordinary skill in the art. A review of methodologies of liposome preparation may be found in Liposome Technology (CFC Press New York 1984); Liposomes by Ostro (Marcel Dekker, 1987); Methods Biochem Anal. 33:337-462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the cationic lipid vaccines of this invention, the cationic lipid is present in the liposome at from about 10 mole % to about 100 mole % of total liposomal lipid, or from about 20 mole % to about 80 mole %. The neutral lipid, when included in the liposome, may be present at a concentration of from about 0 mole % to about 90 mole % of the total liposomal lipid, or from about 20 mole % to about 80 mole %, or from 40 mole % to 80 mole %. The negatively charged lipid, when included in the liposome, may be present at a concentration ranging from about 0 mole % to about 49 mole % of the total liposomal lipid, or from about 0 mole % to about 40 mole %. In one embodiment, the liposomes contain a cationic and a neutral lipid, in ratios between about 2:8 to about 6:4. It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Furthermore, to modify the circulatory half-life of the complexes, the positive surface charge can be sterically shielded by incorporating lipophilic surfactants which contain polyethylene glycol moieties.

The cationic lipid vaccines may be stored in isotonic sucrose or dextrose solution upon collection from the sucrose gradient or they may be lyophilized and then reconstituted in an isotonic solution prior to use. In one embodiment, the cationic lipid complexes are stored in solution. The stability of the cationic lipid complexes of the present invention is measured by specific assays to determine the physical stability and biological activity of the cationic lipid vaccines over time in storage. The physical stability of the cationic lipid vaccines is measured by determining the diameter and charge of the cationic lipid complexes by methods known to those of ordinary skill in the art, including for example, electron microscopy, gel filtration chromatography or by means of quasi-elastic light scattering using, for example, a Coulter N4SD particle size analyzer as described in the Examples. The physical stability of the cationic lipid complex is "substantially unchanged" over storage when the diameter of the stored cationic lipid vaccines is not increased by more than 100%, or by not more than 50%, or by not more than 30%, over the diameter of the cationic lipid complexes as determined at the time the cationic lipid vaccines were purified.

While it is possible for the cationic lipid to be administered in a pure or substantially pure form, it is preferable to present it as a pharmaceutical composition, formulation or preparation. Pharmaceutical formulations using the chiral cationic lipid complexes of the invention may comprise the cationic lipid vaccines in a physiologically compatible sterile buffer such as, for example, phosphate buffered saline, isotonic saline or low ionic strength buffer such as acetate or Hepes (an exemplary pH being in the range of about 5.0 to about 8.0). The chiral cationic lipid vaccines may be administered as aerosols or as liquid solutions for intratumoral, intraarterial, intravenous, intratracheal, intraperitoneal, subcutaneous, and intramuscular administration.

The formulations of the present invention may incorporate any stabilizer known in the art. Illustrative stabilizers are cholesterol and other sterols that may help rigidify the liposome bilayer and prevent disintegration or destabilization of the bilayer. Also agents such as polyethylene glycol, poly-, and mono-saccahrides may be incorporated into the liposome to modify the liposome surface and prevent it from being destabilized due to interaction with blood-components. Other illustrative stabilizers are proteins, saccharides, inorganic acids, or organic acids which may be used either on their own or as admixtures.

A number of pharmaceutical methods may be employed to control, modify, or prolong the duration of immune stimulation. Controlled release preparations may be achieved through the use of polymer complexes such as polyesters, polyamino acids, methylcellulose, polyvinyl, poly(lactic acid), and hydrogels to encapsulate or entrap the cationic lipids and slowly release them. Similar polymers may also be used to adsorb the liposomes. The liposomes may be contained in emulsion formulations in order to alter the release profile of the stimulant. Alternatively, the duration of the stimulant's presence in the blood circulation may be enhanced by coating the surface of the liposome with compounds such as polyethylene glycol or other polymers and other substances such as saccharides which are capable of enhancing the circulation time or half-life of liposomes and emulsions.

When oral preparations are required, the chiral cationic lipids may be combined with typical pharmaceutical carriers known in the art such as, for example, sucrose, lactose, methylcellulose, carboxymethyl cellulose, or gum Arabic, among others. The cationic lipids may also be encapsulated in capsules or tablets for systemic delivery.

Administration of the chiral cationic lipid compositions of the present disclosure may be for either a prophylactic or therapeutic purpose. When provided prophylactically, the cationic lipid is provided in advance of any evidence or symptoms of illness. When provided therapeutically, the cationic lipid is provided at or after the onset of disease. The therapeutic administration of the immune-stimulant serves to attenuate or cure the disease. For both purposes, the cationic lipid may be administered with an additional therapeutic agent(s) or antigen(s). When the cationic lipids are administered with an additional therapeutic agent or antigen, the prophylactic or therapeutic effect may be generated against a specific disease, including for example, disease or disorders caused by HPV.

The formulations of the present invention, both for veterinary and for human use, comprise a pure chiral cationic lipid alone as described above, as a mixture of R and S enantiomers, with one or more therapeutic ingredients such as an antigen(s) or drug molecule(s). The formulations may conveniently be presented in unit dosage form and may be prepared by any method known in the pharmaceutical art.

Terms

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

As used herein, the terms "subject" and "patient" are used interchangeably and include a mammal, e.g., a human, mouse, rat, guinea pig, dog, cat, horse, cow, pig, or non-human primate, such as a monkey, chimpanzee, baboon or gorilla.

As used herein, the terms "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The compositions of the disclosure comprise an amount of a composition of HPV peptides that is effective for generating an immunogenic response in a subject. Specifically, the dosage of the composition to achieve a therapeutic effect will depend on factors such as the formulation, pharmacological potency of the composition, age, weight and sex of the patient, condition being treated, severity of the patient's symptoms, route of delivery, and response pattern of the patient. It is also contemplated that the treatment and dosage of the compositions may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the therapeutic effect. Further, one of skill in the art would be able to calculate any changes in effective amounts of the compositions due to changes in the composition components or dilutions. In one embodiment, the compositions may be diluted 2-fold. In another embodiment, the compositions may be diluted 4-fold. In a further embodiment, the compositions may be diluted 8-fold.

The effective amount of the compositions disclosed herein may, therefore, be about 1 mg to about 1000 mg per dose based on a 70 kg mammalian, for example human, subject.

In another embodiment, the therapeutically effective amount is about 2 mg to about 250 mg per dose. In a further embodiment, the therapeutically effective amount is about 5 mg to about 100 mg. In yet a further embodiment, the therapeutically effective amount is about 25 mg to 50 mg, about 20 mg, about 15 mg, about 10 mg, about 5 mg, about 1 mg, about 0.1 mg, about 0.01 mg, about 0.001 mg.

The effective amounts (if administered therapeutically) may be provided on regular schedule, i.e., on a daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every 2 weeks, about every 3 weeks, about every month, about every 2 months, about every 3 months and about every 6 months. The number and frequency of dosages corresponding to a completed course of therapy will be determined according to the judgment of a health-care practitioner.

The compositions may be administered by any route, taking into consideration the specific condition for which it has been selected. The compositions may be delivered orally, by injection, inhalation (including orally, intranasally and intratracheally), ocularly, transdermally (via simple passive diffusion formulations or via facilitated delivery using, for example, iontophoresis, microporation with microneedles, radio-frequency ablation or the like), intravascularly, cutaneously, subcutaneously, intramuscularly, sublingually, intracranially, epidurally, rectally, intravesically, and vaginally, among others.

The compositions may be formulated neat or with one or more pharmaceutical carriers and/or excipients for administration. The amount of the pharmaceutical carrier(s) is determined by the solubility and chemical nature of the peptides, chosen route of administration and standard pharmacological practice. The pharmaceutical carrier(s) may be solid or liquid and may incorporate both solid and liquid carriers/matrices. A variety of suitable liquid carriers is known and may be readily selected by one of skill in the art. Such carriers may include, e.g., dimethylsulfoxide (DMSO), saline, buffered saline, cyclodextrin, hydroxypropylcyclodextrin (HPβCD), n-dodecyl-β-D-maltoside (DDM) and mixtures thereof. Similarly, a variety of solid (rigid or flexible) carriers and excipients are known to those of skill in the art.

Although the compositions may be administered alone, they may also be administered in the presence of one or more pharmaceutical carriers that are physiologically compatible. The carriers may be in dry or liquid form and must be pharmaceutically acceptable. Liquid pharmaceutical compositions may be sterile solutions or suspensions. When liquid carriers are utilized, they may be sterile liquids. Liquid carriers may be utilized in preparing solutions, suspensions, emulsions, syrups and elixirs. In one embodiment, the compositions may be dissolved a liquid carrier. In another embodiment, the compositions may be suspended in a liquid carrier. One of skill in the art of formulations would be able to select a suitable liquid carrier, depending on the route of administration. The compositions may alternatively be formulated in a solid carrier. In one embodiment, the composition may be compacted into a unit dose form, i.e., tablet or caplet. In another embodiment, the composition may be added to unit dose form, i.e., a capsule. In a further embodiment, the composition may be formulated for administration as a powder. The solid carrier may perform a variety of functions, i.e., may perform the functions of two or more of the excipients described below. For example, a solid carrier may also act as a flavoring agent, lubricant, solubilizer, suspending agent, filler, glidant, compression aid, binder, disintegrant, or encapsulating material. In one embodiment, a solid carrier acts as a lubricant, solubilizer, suspending agent, binder, disintegrant, or encapsulating material. The composition may also be sub-divided to contain appropriate quantities of the compositions. For example, the unit dosage can be packaged compositions, e.g., packeted powders, vials, ampoules, prefilled syringes or sachets containing liquids.

In an embodiment, the compositions may be administered by a modified-release delivery device. "Modified-release" as used herein refers to delivery of the disclosed compositions which is controlled, for example over a period of at least about 8 hours (e.g., extended delivery) to at least about 12 hours (e.g., sustained delivery). Such devices may also permit immediate release (e.g., therapeutic levels achieved in under about 1 hour, or in less than about 2 hours). Those of skill in the art know suitable modified-release delivery devices.

Also provided are kits comprising the compositions disclosed herein. The kit may further comprise packaging or a container with the compositions formulated for the delivery route. Suitably, the kit contains instructions on dosing and an insert regarding the compositions.

A number of packages or kits are known in the art for dispensing pharmaceutical compositions for periodic use. In one embodiment, the package has indicators for each period. In another embodiment, the package is a foil or blister package, labeled ampoule, vial or bottle.

The packaging means of a kit may itself be geared for administration, such as an inhaler, syringe, pipette, eye dropper, catheter, cytoscope, trocar, cannula, pressure ejection device, or other such apparatus, from which the formulation may be applied to an affected area of the body, such as the lungs, injected into a subject, delivered to bladder tissue or even applied to and mixed with the other components of the kit.

One or more components of these kits also may be provided in dried or lyophilized forms. When reagents or components are provided as a dried form, reconstitution generally is by the addition of a suitable solvent. It is envisioned that the solvent also may be provided in another package. The kits may include a means for containing the vials or other suitable packaging means in close confinement for commercial sale such as, e.g., injection or blow-molded plastic containers into which the vials are retained. Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper, catheter, cytoscope, trocar, cannula, pressure-delivery device or any such medically approved delivery means.

The term "treat", "treating", or any variation thereof is meant to include therapy utilized to remedy a health problem or condition in a patient or subject. In one embodiment, the health problem or condition may be eliminated permanently or for a short period of time. In another embodiment, the severity of the health problem or condition, or of one or more symptoms characteristic of the health problem or condition, may be lessened permanently, or for a short period of time. The effectiveness of a treatment of pain can be determined using any standard pain index, such as those described herein, or can be determined based on the patient's subjective pain. A patient is considered "treated" if there is a reported reduction in pain or a reduced reaction to stimuli that should cause pain.

This invention is further illustrated by the following examples, which are not to be construed in any way as imposing limitations upon the scope thereof. On the contrary, it is to be clearly understood that resort may be had to various other embodiments, modifications, and equivalents thereof. which, after reading the description herein, may suggest themselves to those skilled in the art without departing from the spirit of the present invention.

EXAMPLES

Examples are provided below to facilitate a complete understanding of the invention. To date, to facilitate the development of peptide vaccines with broad patient coverage, the vaccines have been developed to contain overlapping peptide sequences of 15-30 amino acids covering the entire protein sequence of HPV. Despite the availability of in-silico peptide binding analysis capable of determining peptide binding to various HLA molecules, this approach has been sparingly utilized to design HLA-independent vaccines, because it is well established that not all peptides that are capable of binding to MHC molecules are naturally processed intracellularly, and the actual HLA coverage may be significantly lower than predicted.

Therefore, to successfully develop a simple HPV therapeutic vaccine that can provide broad patient coverage without utilizing a large number of peptides and without the need to fully represent the entire E6 and E7 protein sequences in the vaccine, an alternative approach was necessary. The first step in the process developed herein to design the simpler formulation was the design of several libraries of peptides from the HPV16 E6 and E7 proteins. The next step was to perform extensive in-vivo studies to screen the peptides to confirm or understand the ability of the immune system to correctly process the specific peptides and to present the right T-cell epitopes via MHC Class I and Class II to CD8+ and CD4+ T-cells respectively. The only way to accurately obtain this information is through actual in-vivo studies to evaluate the T-cell response.

In this study, T-cell response was evaluated by tumor regression studies using the TC-1 tumor model in C57/B6 mice and by interferon-gamma ELISPOT studies in HLA-A2 humanized transgenic mice. The next step was selection of the suitable or preferred peptides based on the resulting T-cell immune responses, and the elimination of sequences that resulted in no T-cell responses or very weak T-cell responses. The selected active peptides were then analyzed by in-silico binding analysis to determine their binding affinity to various HLA molecules. At the end of the analysis, combining the in-vivo data and in-silico analysis, the goal was then to select the minimum number of active peptide sequences derived from the in-vivo studies that when used in combination would be predicted by the in-silico analysis to cover at least 90% of the human population. Finally, the selected peptides were combined into a vaccine formulation. This formulation was then tested for T-cell induction efficacy to ensure that due to competition for binding sites, that the potency of any selected sequence had not been substantially diminished and that T-cell responses to all included peptides could still be obtained, Finally, the predicted breadth of coverage was confirmed in a human clinical trial.

Sequence selection was accomplished herein using both tumor regression studies in C57/B6 mice, and interferon-gamma ELISPOT studies in HLA-A2 humanized transgenic mice. In the peptide evaluation studies performed using tumor regression, a positive T-cell response was a T-cell response that resulted in regression of the tumor. In the HLA-A2 mouse model ELISPOT study, at least 20 spots per million splenocytes was regarded to be a positive response.

Provided herein are summary results showing positive or negative T-cell responses. The details provided enable anyone familiar with the field to understand the necessity for extensive screening of peptide sequences by in-vivo means as a first step, and to follow and replicate all the steps of the invention.

Also provided herein is an illustration showing that peptide HLA-binding prediction by in-silico binding analysis confirms and corresponds to at least 90% patient coverage. These illustrations will enable anyone knowledgeable in the field to correctly follow the process of first selecting the E6 and E7 peptide sequences that may be immunogenic, secondly testing them in-vivo to confirm processing and presentation. Thirdly the selected sequences that are shown in-vivo to be suitably immunogenic are selected and less immunogenic sequences eliminated. Fourth the peptides are subjected to in-silico binding analysis to determine each peptide's binding affinity to various HLA types. Finally a combination of peptides that are predicted to provide at least 90% coverage is selected. In our case a human clinical study was performed to test and confirm the predictions.

The following examples illustrate the exemplary modes of making and practicing the invention. However, the scope of the invention is not limited to specific embodiments disclosed in these Examples, which are illustrative only, since alternative methods can be utilized to obtain similar results. The peptide sequences used in illustrating the invention are provided in Table 1.

TABLE 1

A Sample Of Peptide Sequences Screened In-Vivo And Resulting Immune Response

| Sequence ID | Sequence | Corresponding to | Immune Response, Method |
|---|---|---|---|
| SEQ ID NO: 1 | RAHYNIVTF | E7 49-57 | Positive, tumor regression |
| SEQ ID NO: 2* | DRAHYNIVTF | E7 48-57 | Negative, tumor regression |
| SEQ ID NO: 3 | PalmKSS RAHYNIVTF | E7 49-57 | Positive, tumor regression |

TABLE 1 -continued

A Sample Of Peptide Sequences Screened In-Vivo And Resulting Immune Response

| Sequence ID | Sequence | Corresponding to | Immune Response, Method |
|---|---|---|---|
| SEQ ID NO: 4 | KSS RAHYNIVTF | E7 49-57 | Positive, tumor regression |
| SEQ ID NO: 5 | GQAEPDRAHYNIVTF | E7 43-57 | Positive, tumor regression |
| SEQ ID NO: 6* | KSS GQAEPDRAHYNIVTF | E7 43-57 | Negative, tumor regression |
| SEQ ID NO: 7 | PAGQAEPDRAHYNIVTFC | E7 41-58 | Positive, tumor regression |
| SEQ ID NO: 8* | EPDRAHYNIVTFCCKCDS | E7 46-63 | Negative, tumor regression |
| SEQ ID NO: 9 | MHGDTPTLHEYMLDLQPETT | E7 1-20 | Positive, EISPOT |
| SEQ ID NO: 10 | LLMGTLGIVCPICSQKP | E7 82-98 | Positive, ELISPOT |
| SEQ ID NO: 11 | ELQTTIHDIILECVYCKQQLL | E6 25-45 | Positive, ELISPOT |
| SEQ ID NO: 12* | KFYSKISEYRHCYYSLYGTTL | E7 75-95 | Negative, ELISPOT |
| SEQ ID NO: 13* | QQLLRREVYDFAFRDLCIVYR | E7 42-62 | Negative, ELISPOT |
| SEQ ID NO: 14 | YMLDLQPETT | E7 11-20 | Positive, ELISPOT |
| SEQ ID NO: 15 | LLMGTLGIV | E7 82-90 | Positive, ELISPOT |
| SEQ ID NO: 16 | IVCPICSQK | E7 89-96 | Evaluated as epitope |
| SEQ ID NO: 17 | GTLGIVCPI | E7 85-92 | Evaluated as epitope |
| SEQ ID NO: 18 | IILECVYCK | E6 33-41 | Evaluated as epitope |
| SEQ ID NO: 19 | TLHEYMLDL | E7 7-15 | Evaluated as epitope |
| SEQ ID NO: 20 | TPTLHEYML | E7 5-13 | Evaluated as epitope |
| SEQ ID NO: 21 | TIHDIILECV | E7 29-38 | Positive, ELISPOT |
| SEQ ID NO: 22 | TLGIVCPIC | E7 86-93 | Positive, ELISPOT |
| SEQ ID NO: 23 | PalmKSS ELQTTIHDIILECVYCKQQLL | E6 25-45 | Positive, ELISPOT |
| SEQ ID NO: 24 | PalmKSS MHGDTPTLHEYMLDLQPETT | E7 1-20 | Positive, ELISPOT |
| SEQ ID NO: 25 | PalmKSS LLMGTLGIVCPICSQKP | E7 82-98 | Positive, ELISPOT |
| SEQ ID NO: 26 | PalmKSS GQAEPDRAHYNIVTF | E7 43-57 | Positive tumor regression |
| SEQ ID NO: 26 | PalmKSS GQAEPDRAHYNIVTF | E7 43-57 | Positive, ELISPOT |
| SEQ ID NO: 27 | PalmKSS YMLDLQPETT | E7 11-20 | Positive, ELISPOT |
| SEQ ID NO: 28 | PalmKSS LLMGTLGIV | E7 82-90 | Positive, ELISPOT |
| SEQ ID NO: 29 | FAFRDLCIV | E7 52-60 | Evaluated as epitope |
| SEQ ID NO: 30 | KISEYRHCY | E7 79-87 | Evaluated as epitope |
| SEQ ID NO: 31 | RLCVQ STHVDIRTLEDLL | E7 66-83 | Evaluated for formulation |
| SEQ ID NO: 32 | CDSTLRLCVQ STHVDIRT | E7 61-78 | Positive, tumor formulation |

*Does not meet the efficacy criteria for selection to evaluate in binding studies

Example 1

Peptide Sequence Screening by TC-1 Tumor Regression in C57/B6 Mice

This example illustrates the evaluation or screening of several HPV16 E7 peptides in the TC-1 mouse tumor regression model for their effective processing and presentation of the key epitopes leading to HPV-specific T-cell induction and subsequent tumor regression.

In the tumor regression screening studies mice were implanted with 100,000 TC-1 cells on day 0. On day 7, once the tumors were well established the mice were vaccinated with the specific peptide sequences, either formulated alone or in combination with cationic lipids such as DOTMA, DOEPC or R-DOTAP to facilitate up-take and presentation. In these studies, the vaccine contained the selected peptide at a concentration of 0.1-3.0 mg/mL and cationic liposomes at a concentration of 0.2-3.0 mg/mL. In the cases where the peptide sequences were lipidated by attaching a palmitoyl chain, the peptides were simply mixed with the cationic liposomes prior to vaccination. In the case of the non-lipidated peptides, the liposomes were made and peptides encapsulated by traditional thin film liposome preparation methods (F Szoka, and D Papahadjopoulos, *Comparative Properties and Methods of Preparation of Lipid Vesicles (Liposomes)*, Annual Review of Biophysics and Bioengineering, Vol. 9:467-508, 1980). Other methods well known to those skilled in the art may also have been used.

Figure 3:
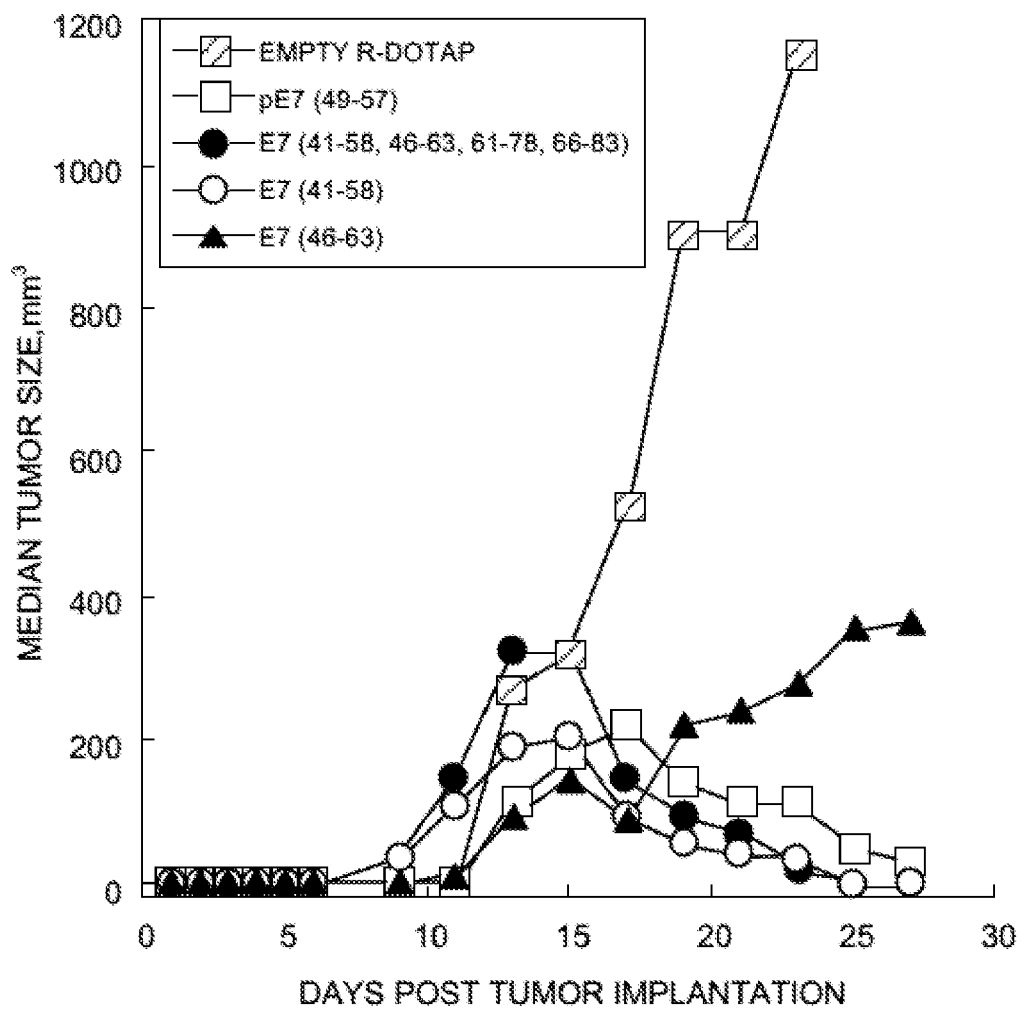
FIG. 3 provides a sample tumor regression plot showing results of the effect of peptides on median tumor size as measured over time following tumor implantation for peptides corresponding to SEQ ID NO: 1 (blank square), SEQ ID NOS: 7, 8, 31 32 and 31 (solid black circle), SEQ ID NO: 7 (blank circle), and SEQ ID NO: 8 (solid black triangle).

A sample tumor regression plot showing results for peptides corresponding to SEQ ID NO: 1 (blank square), SEQ ID NOS: 7, 8, 31 32 and 31 (solid black circle), SEQ ID NO: 7 (blank circle), and SEQ ID NO: 8 (solid black triangle) is shown in FIG. 3. The results highlight the fact that some HPV E7 sequences resulted in effective tumor regression whereas others did not, presumably due to ineffective ability to present the required CD8+ T-cell epitope. Select results are summarized in Table 1.

Example 2

Peptide Sequence Screening by IFN-G ELISPOT Studies in HLA-A2 Mice

This example highlights the approach to evaluating T-cell responses using ELISPOT studies in humanized HLA-A2 transgenic mice. In these studies, the vaccine contained the selected peptide at a concentration of 0.1-3.0 mg/mL and cationic liposomes when used, at a concentration of 0.2-3.0 mg/mL. Humanized HLA-A2 transgenic mice having components of the human immune system capable of recognizing human antigens were vaccinated on day 0 and day 7 with 100 uL of the vaccine. On day 14 the mice were sacrificed and HPV-specific immune response evaluated by interferon-gamma ELISPOT using standard approaches with the splenocytes from the mice (4-8 per group). The splenocytes were stimulated with the specified CD8+ T-cell epitope peptides or the long multi-epitope peptides specified in Table 2. The number of IFN-g spots per million cells is listed for the specified examples. A minimum of 20 spots was the cut-off for adequate potency, and selection for binding epitope binding studies. The ability of the humanized transgenic mice to successfully generate a T-cell immune response (>20 spots) when stimulated with each of the long multi-epitope peptides as well as short single epitope peptides confirms that the selected peptides are effectively processed and presented to T-cells. In these studies, un-stimulated splenocytes and splenocytes stimulated with irrelevant peptides were both used together as negative controls in every assay. For the positive control in the assay ConA was used.

TABLE 2

Summary of IFN-g ELISPOT Studies-selected sequences

| Sequence ID | Sequence | T-cell Epitope Used as Stimulatory peptide | ELISPOT result Av spots/ $10^6$ cells |
|---|---|---|---|
| SEQ ID NO: 9 | MHGDTPTLHEYMLDLQPETT | YMLDLQPETT (SEQ ID NO: 14) | 235 |
| SEQ ID NO: 10 | LLMGTLGIVCPICSQKP | TLGIVCPIC (SEQ ID NO: 22) | 27 |
| SEQ ID NO: 10* | LLMGTLGIVCPICSQKP | LLMGTLGIV (SEQ ID NO: 15) | 1 |
| SEQ ID NO: 11 | ELQTTIHDIILECVYCKQQLL | TIHDIILECV (SEQ ID NO: 21) | 262 |
| SEQ ID NO: 12* | KFYSKISEYRHCYYSLYGTTL | KISEYRHCY (SEQ ID NO: 30) | 15 |
| SEQ ID NO: 13* | QQLLRREVYDFAFRDLCIVYR | FAFRDLCIV (SEQ ID NO: 29) | 6 |
| SEQ ID NO: 14 | YMLDLQPETT | YMLDLQPETT (SEQ ID NO: 14) | 580 |
| SEQ ID NO: 15 | LLMGTLGIV | | |
| SEQ ID NO: 21 | TIHDIILECV | | |
| SEQ ID NO: 23 | PalmKSS ELQTTIHDIILECVYCKQQLL | TIHDIILECV (SEQ ID NO: 21) | 612 |
| SEQ ID NO: 23* | PalmKSS ELQTTIHDIILECVYCKQQLL | ELQTTIHDIILECVYCKQQLL (SEQID NO: 13) | 8 |
| SEQ ID NO: 24 | PalmKSS MHGDTPTLHEYMLDLQPETT | YMLDLQPETT (SEQ ID NO: 14) | 79 |

TABLE 2 -continued

Summary of IFN-q ELISPOT Studies-selected sequences

| Sequence ID | Sequence | T-cell Epitope Used as Stimulatory peptide | ELISPOT result Av spots/ 10⁶ cells |
|---|---|---|---|
| SEQ ID NO: 24 | PalmKSS MHGDTPTLHEYMLDLQPETT | MHGDTPTLHEYMLDLQPETT (SEQ ID NO: 9) | 284 |
| SEQ ID NO: 25* | PalmKSS LLMGTLGIVCPICSQKP | LLMGTLGIV (SEQ ID NO: 15) | 5 |
| SEQ ID NO: 25 | PalmKSS LLMGTLGIVCPICSQKP | TLGIVCPIC (SEQ ID NO: 22) | 31 |
| SEQ ID NO: 25 | PalmKSS LLMGTLGIVCPICSQKP | LLMGTLGIVCPICSQKP (SEQ ID NO: 10) | 92 |
| SEQ ID NO: 26 | PalmKSS GQAEPDRAHYNIVTF | RAHYNIVTF (SEQ ID NO: 1) | 1,552 |
| SEQ ID NO: 26 | PalmKSS GQAEPDRAHYNIVTF | GQAEPDRAHYNIVTF (SEQ ID NO: 5) | 1,544 |
| SEQ ID NO: 27 | PalmKSS YMLDLQPETT | YMLDLQPETT (SEQ ID NO: 14) | 280 |
| SEQ ID NO: 28 | PalmKSS LLMGTLGIV | LLMGTLGIV (SEQ ID NO: 15) | 96 |

*Does not meet the efficacy criteria for selection to evaluate in binding studies Example 3

Effect of Chemical Modifications Such as Oxidation and Multimer Formation of the Selected Sequences on the Immunogenicity of the HPV16 Vaccine The present study was performed to evaluate the effect of chemical modification of select peptides on immunogenicity and their ability to be processed, presented and to prime human CD8+ HPV-specific T-cell responses. Peptides corresponding to SEQ ID NO: 23 and 25 contain cysteines which upon oxidation lead to the formation of dimers and other multimers. Two vaccine formulations were prepared containing peptides corresponding to SEQ ID NO: 23 and 25.

In Formulation A: Both peptides were monomeric with high purity confirmed by HPLC analysis. The vaccine contained 1.5-1.6 mg/mL of each peptide.

In Formulation B: Significant oxidation and multimer formation of both peptides was confirmed by HPLC analysis.

Both formulations were mixed 1:1 with 5.8 mg/mL of R-DOTAP prior to vaccination.

The immunogenicity of the peptides was compared as described in the above examples in 10 HLA-A2 mice per formulation by evaluating the ability to induce CD8+ T-cells. ELISPOT studies were performed as described above. Table 3 below shows the results of the ELISPOT study and comparison using the student's T-test. The results of the statistical analysis indicate that the differences between Formulations A and B do not meet the P-value of P<0.05 for significance. The present study suggests that modifications such as oxidation will not negatively impact the immunogenicity of the peptide sequences.

TABLE 3

Effect of chemical modifications such as oxidation and multimer formation of Peptide Sequences 23 and 25 on the CD8+ T-cell immunogenicity of the peptides

| Sequence ID | Sequence | T-cell Epitope Used as Stimulatory peptide | ELISPOT result Av spots/ 10⁶ cells |
|---|---|---|---|
| Formulation A | | | |
| SEQ ID NO: 23 | PalmKSS ELQTTIH DIILECVYCKQQLL | TIHDIILECV (SEQ ID NO: 21) | 314 |
| SEQ ID NO: 25 | PalmKSS LLMGTLG IVCPICSQKP | LLMGTLGIV (SEQ ID NO: 15) | 52 |
| Formulation B | | | |
| SEQ ID NO: 23 | PalmKSS ELQTTIH DIILECVYCKQQLL | TIHDIILECV (SEQ ID NO: 21) | 158 |
| SEQ ID NO: 25 | PalmKSS LLMGTLG IVCPICSQKP | LLMGTLGIV (SEQ ID NO: 15) | 48 |

SEQ ID NO: 23: Formulation A vs. B - P = 0.08
SEQ ID NO: 25: Formulation A vs. B - P = 0.80

Example 4

Summary of in-Silico Analysis of the Potential HLA Alleles that could Bind HPV Peptides Present in a Multi-Epitope Peptide Vaccine Containing the 4 Selected Peptide Sequences Several HPV16 E6 and E7 peptide sequences were designed and evaluated in vivo in humanized HLA-A2 mice for the ability of the peptides to be effectively processed and specific epitopes presented to prime antigen-specific T-cells as described in the above examples. As would be evident to those skilled in the art, peptide epitope interactions are complex depending on numerous factors including stereochemistry, presence of cofactors and biochemical properties of the environment. Accordingly, selection of appropriate peptides for optimal efficacy in vaccines is neither a routine nor a predictable practice. Based on extensive in-vivo studies to identify suitable peptide sequences that could be effective processed and T-cell epitopes presented, selected peptides were then further selected based upon their ability to induce regression of established tumors or to induce IFN-gamma inducing HPV-specific T-cells, and then analyzed by in-silico binding analysis to evaluate their HLA coverage. The predictions were then confirmed in a human clinical trial.

The HLA supertype, HLA-A2 accounts for about 42% of the population (Sette, A. and J. Sidney, *Nine major HLA class I supertypes account for the vast preponderance of HLA-A and -B polymorphism*. Immunogenetics, 1999. 50(3-4): p. 201-12). HPV16 E6 and E7 express experimentally verified epitopes that can be presented by HLA A2, as well as epitopes that may be presented by other HLA types.

To do this, peptide binding affinities to 9 different HLA molecules representing the 9 major HLA supertypes (Sette, A. and J. Sidney, *HLA supertypes and supermotifs: a functional perspective on HLA polymorphism*. Curr Opin Immunol, 1998. 10(4): p. 478-82) was assessed. The 9 major HLA supertypes account for over 98% of the peptide binding potential of the human population (Sette, A. and J. Sidney, *Nine major HLA class I supertypes account for the vast preponderance of HLA-A and -B polymorphism*. Immunogenetics, 1999. 50(3-4): p. 201-12). The extensive screening in-vivo studies leading to the identification of suitable sequences for evaluation of HLA-binding, as well as confirmatory studies to ensure that competition for binding sites does not diminish the ability of the immune system to process and present specific T-cell epitopes when combined in a vaccine formulation are described throughout the Examples provided herein. The present studies demonstrate that though peptide selection techniques, and peptide screening techniques are available, the process of identifying, selecting and combining the peptides to optimize the process of creating an effective vaccine with broad applicability was neither routine nor straightforward.

TABLE 4

Binding activity for 4 selected peptide sequences post-screening

| Peptide present in the formulation | HLA Super-type | Peptide CD8+ T-cell epitope sequence | IC50 (nM) |
|---|---|---|---|
| SEQ ID NOS: 10 & 25 | HLA-A*03:01 | IVCPICSQK (SEQ ID NO: 16) | 155 |
| SEQ ID NOS: 10 & 25 | HLA-A*02:01 | LLMGTLGIV (SEQ ID NO: 15) | 19 |
| SEQ ID NOS: 10 & 25 | HLA-A*02:01 | GTLGIVCPI (SEQ ID NO: 17) | 155 |
| SEQ ID NOS: 11 & 23 | HLA-A*03:01 | IILECVYCK (SEQ ID NO: 18) | 126 |
| SEQ ID NOS: 5 & 26 | HLA-A*24:02 | RAHYNIVTF (SEQ ID NO: 1) | 1699 |
| SEQ ID NOS: 5 & 26 | HLA-B*58:01 | RAHYNIVTF (SEQ ID NO: 1) | 107 |
| SEQ ID NOS: 9 & 24 | HLA-A*02:01 | YMLDLQPETT (SEQ ID NO: 14) | 5 |
| SEQ ID NOS: 9 & 24 | HLA-A*02:01 | TLHEYMLDL (SEQ ID NO: 19) | 48 |
| SEQ ID NOS: 9 & 24 | HLA-B*07:02 | TPTLHEYML (SEQ ID NO: 20) | 921 |

Table 4 summarizes for the purpose of the disclosure, the result of the peptide binding analysis of the four preferred peptide sequences identified by the T-cell induction studies as well as the possible epitopes covered by those sequences using the epitope prediction tool present in the Immune Epitope Database (www.iedb.org). The tool calculates a predicted binding affinity (IC50) of the peptide with a particular HLA class I allele. An IC50 of 5,000 nM or less is generally reported to be sufficient for biologically relevant binding and presentation with a binding affinity of less than 500 nM considered to represent high affinity binding. In the current analysis 2,000 nM was chosen as a cutoff to assess potential HLA binding peptides. As shown in Table 4, at least 5 different HLA molecules representing 5 distinct HLA supertypes are identified as having the potential for biologically significant binding and presentation of different peptides within SEQ ID NOS: 5, 9, 10 and 11 or 23-26. These 5 supertypes are known to be representative of greater than 90% of the human population irrespective of ethnicity [Sette, A. and J. Sidney, *Nine major HLA class I supertypes account for the vast preponderance of HLA-A and -B polymorphism*. Immunogenetics, 1999. 50(3-4): p. 201-12].

Example 5

Compatibility of Other Cationic Lipids Beyond R-DOTAP with the HPV-E6 and E7 Peptide Sequences and Ability to Induce HPV-Specific T-Cell Responses To determine if the identified long HPV16 peptides are compatible with other cationic lipids besides DOTAP, the peptide corresponding to SEQ ID NO: 26 was used as the model peptide in combination with two other cationic lipids DOTMA and DOEPC. To evaluate the ability of the peptides to effectively undergo processing and presentation, in the presence of both cationic lipids, an ELISPOT study was conducted using normal C57/B6 mice. ELISPOT studies were performed as described above and utilized to determine effective CD8+ T-cell induction.

In formulation 1, 1.35 mg/mL of DOTMA was mixed 1:1 v/v with 0.5 mg/mL of the peptide corresponding to SEQ ID NO: 26.

In formulation 2, 1.67 mg/mL of DOEPC was missed 1:1 v/v with 0.5 mg/mL of the peptide corresponding to SEQ ID NO: 26.

For each formulation 4 mice were vaccinated on Day 0 and Day 7. On Day 14 the mice were scarified and the splenocytes utilized in the ELISPOT study.

TABLE 5

ELISPOT results for HPV-peptide formulations with various cationic lipids

| Sequence ID | Sequence | T-cell Epitope Used as Stimulatory peptide | ELISPOT result Av spots/ $10^6$ cells |
|---|---|---|---|
| DOTMA | | | |
| SEQ ID NO: 26 | PalmKSS GQAEPDRAHYNIVTF | RAHYNIVTF (SEQ ID NO: 1) | 988 |
| DOEPC | | | |
| SEQ ID NO: 26 | PalmKSS GQAEPDRAHYNIVTF | RAHYNIVTF (SEQ ID NO: 1) | 243 |

The study demonstrates that various cationic lipids may be used with the identified HPV E6 and E7 peptides to induce strong HPV-specific T-cell responses.

Example 8

Use of Lipidated Peptides (SEQ ID NOS: 23-28) and R-DOTAP Cationic Lipid in an HPV Therapeutic Vaccine and Evaluation of HPV-Specific T-Cell Responses in a Human Clinical Trial The 6-peptide formulation containing the 4 peptides (SEQ. ID NOS: 23-26) that were projected in Examples 1-4 to cover >90% of the population based on in-vivo T-cell responses and peptide binding, and 2 additional single epitope peptides (SEQ ID NOS: 27 and 28) already contained in SEQ ID NOS: 24 and 25 was evaluated in a human clinical trial (clinical trials.gov #NCT02065973). The 2 single epitope peptides included in the formulation provide no additional coverage since they are already contained in 2 of the included long peptide sequences.

In this exploratory study, due to the variable nature of biological systems and human responses, the immune response to the vaccine was evaluated by both IFN-γ and granzyme-b ELISPOT. Each subject was given 3 vaccinations of the R-DOTAP/peptide formulation. All subjects were given 3 vaccinations, 1 every 3 weeks. Blood was taken pre-vaccination (Baseline) and 14-19 days after each vaccination and at 90 days after the last vaccination for immune monitoring by ELISPOT. The subjects were not restricted by HLA-type in order to confirm the broad coverage of the vaccine. The ELISPOT analysis was performed using the subject PBMCs and stimulated with the 6-peptide mixture to determine effective presentation and T-cell recognition of the HPV-peptides.

The results for the human clinical study are shown in Table 6 below. A vaccine-induced response is typically defined as 2 or 3-fold increase in immune response over baseline. In this study, an immune response was defined as a 3-fold or greater increase in T-cell response post-vaccination compared to the baseline sample by either IFN-γ or granzyme-b analysis. Two subjects, subjects 2 and 5 both of whom had very strong T-cell responses of over 420 IFN-g spots (immune systems possibly already responding to a recent HPV infection) at baseline were considered to be outliers (Table 6). All subjects were tested for HLA-type. Half of the subjects were HLA-A2 as expected, as this is the most common HLA-type. However, all subjects including the non-HLA-A2 subjects (HLA-A1, 30, 3, 74, 80 etc.) generated strong T-cell responses to the vaccine. The study confirmed that the combination of the 4 multi-epitope peptides, SEQ ID NOS: 23-26 provide a broadly applicable human HPV16 vaccine which can be recognized by patients of varying genetic backgrounds.

TABLE 6

Evaluation Of The Ability Of An HPV16 Vaccine Formulation Containing A Cationic Lipid And Peptide (SEQ ID NO: 23-28) To Prime Antigen-Specific T-Cells Including CD8+ T-Cells By INF-Γ And Granzyme-B ELISPOT In Human Subjects With Varying HLA Types Mean number of spots per 400,000 cells

| | | IFN-γ | | Granzyme-b | | |
|---|---|---|---|---|---|---|
| Patient[#]* | HLA-type | Base-line** | Factor increase over baseline*** | Base-line** | Factor increase over baseline*** | Active |
| 1 | 02 | 6.0 | 19.7 | N/A | | Yes |
| 2 | 01, 02 | 423.0 | | Outlier | | |
| 3 | 01 | 69.5 | 7.3 | 5.7 | 3.0 | Yes |
| 4 | 02 | 22.0 | 14.8 | 0.0 | 10.3 | Yes |
| 5 | 29 | 464.7 | | Outlier | | |
| 6 | 03 | 17.8 | 32.8 | 6.7 | 31.8 | Yes |
| 7 | 02, 26 | 3.0 | 4.8 | 51.3 | 1.2 | Yes |
| 8 | 02, 68 | 1.0 | 72.7 | 8.0 | 7.6 | Yes |
| 9 | 03 | 2.3 | 10.4 | 10.0 | 1.0 | Yes |
| 10 | 74, 80 | 1.0 | 53.3 | 1.0 | 61.3 | Yes |
| 11 | 02, 30 | 9.0 | 1.4 | 1.0 | 35 | Yes |
| 12 | N/A | 1.0 | 10.7 | 23.3 | 1.1 | Yes |
| Average response | | | 22.8 | | 15.2 | |

*Baseline is visit 2 (pre-vaccination visit) counts minus the Background counts
**Maximum response is maximum response (counts) observed in the subject minus the Background counts
***Factor increase over Baseline is the Maximum response divided by Baseline counts (Factor of ≥3 is considered to be an immune response due to vaccination[4,5])
****A negative result resulting from Counts minus Background is given the value of 0, and 0/0 = 0
[#]Active: Factor increase over Baseline of ≥3 by IFN-γ and/or Granzyme-b ELISPOT

---

SEQUENCE LISTING

<160> NUMBER OF SEQ ID NOS: 32

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Arg Ala His Tyr Asn Ile Val Thr Phe 1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Asp Arg Ala His Tyr Asn Ile Val Thr Phe
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Synthetic

<400> SEQUENCE: 3

Pro Ala Leu Met Lys Ser Ser Arg Ala His Tyr Asn Ile Val Thr Phe
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Lys Ser Ser Arg Ala His Tyr Asn Ile Val Thr Phe
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Synthetic

<400> SEQUENCE: 5

Gly Gln Ala Glu Pro Asp Arg Ala His Tyr Asn Ile Val Thr Phe
1               5                   10                  15

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Lys Ser Ser Gly Gln Ala Glu Pro Asp Arg Ala His Tyr Asn Ile Val
1               5                   10                  15

Thr Phe

<210> SEQ ID NO 7
<211> LENGTH: 18
<212> TYPE: PRT
<213> ORGANISM: Artificial Sequence
<220> FEATURE:
<223> OTHER INFORMATION: Synthetic

<400> SEQUENCE: 7

```
Pro Ala Gly Gln Ala Glu Pro Asp Arg Ala His Tyr Asn Ile Val Thr
1               5                   10                  15

Phe Cys

<210> SEQ ID NO 8
<211> LENGTH: 18
<212> TYPE: PRT
<213> ORGANISM: Artificial Sequence
<220> FEATURE:
<223> OTHER INFORMATION: Synthetic

<400> SEQUENCE: 8

Glu Pro Asp Arg Ala His Tyr Asn Ile Val Thr Phe Cys Cys Lys Cys
1               5                   10                  15

Asp Ser

<210> SEQ ID NO 9
<211> LENGTH: 20
<212> TYPE: PRT
<213> ORGANISM: Artificial Sequence
<220> FEATURE:
<223> OTHER INFORMATION: Synthetic

<400> SEQUENCE: 9

Met His Gly Asp Thr Pro Thr Leu His Glu Tyr Met Leu Asp Leu Gln
1               5                   10                  15

Pro Glu Thr Thr
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic

<400> SEQUENCE: 10

Leu Leu Met Gly Thr Leu Gly Ile Val Cys Pro Ile Cys Ser Gln Lys
1               5                   10                  15

Pro

<210> SEQ ID NO 11
<211> LENGTH: 21
<212> TYPE: PRT
<213> ORGANISM: Artificial Sequence
<220> FEATURE:
<223> OTHER INFORMATION: Synthetic

<400> SEQUENCE: 11

Glu Leu Gln Thr Thr Ile His Asp Ile Ile Leu Glu Cys Val Tyr Cys
1               5                   10                  15

Lys Gln Gln Leu Leu
            20

<210> SEQ ID NO 12
<211> LENGTH: 21
<212> TYPE: PRT
<213> ORGANISM: Artificial Sequence
<220> FEATURE:
<223> OTHER INFORMATION: Synthetic

<400> SEQUENCE: 12

Lys Phe Tyr Ser Lys Ile Ser Glu Tyr Arg His Cys Tyr Tyr Ser Leu
1               5                   10                  15
```

Tyr Gly Thr Thr Leu
            20

<210> SEQ ID NO 13
<211> LENGTH: 21
<212> TYPE: PRT
<213> ORGANISM: Artificial Sequence
<220> FEATURE:
<223> OTHER INFORMATION: Synthetic

<400> SEQUENCE: 13

Gln Gln Leu Leu Arg Arg Glu Val Tyr Asp Phe Ala Phe Arg Asp Leu
1               5                   10                  15

Cys Ile Val Tyr Arg
            20

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Tyr Met Leu Asp Leu Gln Pro Glu Thr Thr
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Leu Leu Met Gly Thr Leu Gly Ile Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ile Val Cys Pro Ile Cys Ser Gln Lys
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Gly Thr Leu Gly Ile Val Cys Pro Ile
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

```
<400> SEQUENCE: 18

Ile Ile Leu Glu Cys Val Tyr Cys Lys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Thr Leu His Glu Tyr Met Leu Asp Leu
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Thr Pro Thr Leu His Glu Tyr Met Leu
1               5

<210> SEQ ID NO 21
<211> LENGTH: 10
<212> TYPE: PRT
<213> ORGANISM: Artificial Sequence
<220> FEATURE:
<223> OTHER INFORMATION: Synthetic

<400> SEQUENCE: 21

Thr Ile His Asp Ile Ile Leu Glu Cys Val
1               5                   10

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Thr Leu Gly Ile Val Cys Pro Ile Cys
1               5

<210> SEQ ID NO 23
<211> LENGTH: 28
<212> TYPE: PRT
<213> ORGANISM: Artificial Sequence
<220> FEATURE:
<223> OTHER INFORMATION: Synthetic

<400> SEQUENCE: 23

Pro Ala Leu Met Lys Ser Ser Glu Leu Gln Thr Thr Ile His Asp Ile
1               5                   10                  15

Ile Leu Glu Cys Val Tyr Cys Lys Gln Gln Leu Leu
            20                  25

<210> SEQ ID NO 24
<211> LENGTH: 27
<212> TYPE: PRT
<213> ORGANISM: Artificial Sequence
```

<220> FEATURE:
<223> OTHER INFORMATION: Synthetic

<400> SEQUENCE: 24

Pro Ala Leu Met Lys Ser Ser Met His Gly Asp Thr Pro Thr Leu His
1               5                   10                  15

Glu Tyr Met Leu Asp Leu Gln Pro Glu Thr Thr
            20                  25

<210> SEQ ID NO 25
<211> LENGTH: 24
<212> TYPE: PRT
<213> ORGANISM: Artificial Sequence
<220> FEATURE:
<223> OTHER INFORMATION: Synthetic

<400> SEQUENCE: 25

Pro Ala Leu Met Lys Ser Ser Leu Leu Met Gly Thr Leu Gly Ile Val
1               5                   10                  15

Cys Pro Ile Cys Ser Gln Lys Pro
            20

<210> SEQ ID NO 26
<211> LENGTH: 22
<212> TYPE: PRT
<213> ORGANISM: Artificial Sequence
<220> FEATURE:
<223> OTHER INFORMATION: Synthetic

<400> SEQUENCE: 26

Pro Ala Leu Met Lys Ser Ser Gly Gln Ala Glu Pro Asp Arg Ala His
1               5                   10                  15

Tyr Asn Ile Val Thr Phe
            20

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Pro Ala Leu Met Lys Ser Ser Tyr Met Leu Asp Leu Gln Pro Glu Thr
1               5                   10                  15

Thr

<210> SEQ ID NO 28
<211> LENGTH: 16
<212> TYPE: PRT
<213> ORGANISM: Artificial Sequence
<220> FEATURE:
<223> OTHER INFORMATION: Synthetic

<400> SEQUENCE: 28

Pro Ala Leu Met Lys Ser Ser Leu Leu Met Gly Thr Leu Gly Ile Val
1               5                   10                  15

<210> SEQ ID NO 29
<211> LENGTH: 9
<212> TYPE: PRT
<213> ORGANISM: Artificial Sequence
<220> FEATURE:
<223> OTHER INFORMATION: Synthetic

```
<400> SEQUENCE: 29

Phe Ala Phe Arg Asp Leu Cys Ile Val
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Lys Ile Ser Glu Tyr Arg His Cys Tyr
1               5

<210> SEQ ID NO 31
<211> LENGTH: 18
<212> TYPE: PRT
<213> ORGANISM: Artificial Sequence
<220> FEATURE:
<223> OTHER INFORMATION: Synthetic

<400> SEQUENCE: 31

Arg Leu Cys Val Gln Ser Thr His Val Asp Ile Arg Thr Leu Glu Asp
1               5                   10                  15

Leu Leu

<210> SEQ ID NO 32
<211> LENGTH: 18
<212> TYPE: PRT
<213> ORGANISM: Artificial Sequence
<220> FEATURE:
<223> OTHER INFORMATION: Synthetic

<400> SEQUENCE: 32

Cys Asp Ser Thr Leu Arg Leu Cys Val Gln Ser Thr His Val Asp Ile
1               5                   10                  15

Arg Thr
```

What is claimed:

1. A CD8+ T-cell activating HPV therapeutic vaccine composition comprising peptide antigens and an adjuvant,
   wherein the peptide antigens consist of four different long HPV peptides: a peptide comprising SEQ ID NO: 5, a peptide comprising SEQ ID NO: 9, a peptide comprising SEQ ID NO: 10, and a peptide comprising SEQ ID NO: 11, or lipidated versions thereof,
   wherein each individual peptide has a binding affinity of approximately IC50 of 5,000 nM with 5 HLA supertypes, wherein the peptides are multi-epitope peptides, and wherein the adjuvant comprises a cationic lipid.

2. The composition of claim 1, wherein the cationic lipid consists of DOTAP, DDA, DOEPC, DOTMA, R-DOTAP, R-DDA, R-DOEPC, R-DOTMA, S-DOTAP, S-DDA, S-DOEPC, S-DOTMA, variations or analogs thereof.

3. The composition of claim 1, wherein the HLA supertypes consist of HLA-A*02:01, HLA-A*03:01, HLA-A*24:02, HLA-B*07:02, and HLA-B*58:01.

4. The composition of claim 1, wherein the peptides comprise modified peptides.

5. The composition of claim 4, wherein the peptides are oxidized, cross-linked by di-sulfide bonds, pegylated, glycosylated, phosphorylated, palmitoylated, methylated, or biotinylated.

6. The composition of claim 1, wherein the peptides consist of SEQ ID NOS: 5, 9, 10, 11, 23, 24, 25 or 26, and wherein the cationic lipid comprises R-DOTAP.

7. The composition of claim 2, wherein the peptides are encapsulated in liposomes comprising cationic lipids.

8. A method of inducing an immune response against HPV infection in a subject comprising administering to a subject the vaccine composition of claim 1.

9. The method of claim 8, wherein the adjuvant comprises a cationic lipid consisting of DOTAP, DDA, DOEPC, DOTMA, R-DOTAP, R-DDA, R-DOEPC, R-DOTMA, S-DOTAP, S-DDA, S-DOEPC, S-DOTMA, variations or analogs thereof.

10. The method of claim 8, wherein the cationic lipid consists of R-DOTAP.

* * * * *

UNITED STATES PATENT AND TRADEMARK OFFICE
CERTIFICATE OF CORRECTION

PATENT NO.      : 11,401,306 B2
APPLICATION NO. : 15/724818
DATED           : August 2, 2022
INVENTOR(S)     : Frank Bedu-Addo et al.

It is certified that error appears in the above-identified patent and that said Letters Patent is hereby corrected as shown below:

In the Specification

Column 1, Line 5, add the below new paragraph before "TECHNICAL FIELD" after the Title as follows:
SEQUENCE LISTING
This application includes an electronically submitted sequence listing in ASCII format and is hereby incorporated by reference in its entirety. Said ASCII copy, created on March 27, 2024, is named "PDS-17-1274R_SL.txt" and is 8,821 bytes in size.

SEQUENCE LISTING, following Column 31 and 32, delete SEQUENCE ID NO 3 and replace with SEQUENCE ID NO 3 as follows:

```
<210> SEQ ID NO 3
<211> LENGTH: 12
<212> TYPE: PRT
<213> ORGANISM: Artificial Sequence
<220> FEATURE
<223> OTHER INFORMATION: Synthetic

<400> SEQUENCE: 3

Lys Ser Ser Arg Ala His Tyr Asn Ile Val Thr Phe
1               5                   10
```

Signed and Sealed this
Twenty-seventh Day of August, 2024

*Katherine Kelly Vidal*

Katherine Kelly Vidal
*Director of the United States Patent and Trademark Office*

CERTIFICATE OF CORRECTION (continued)
U.S. Pat. No. 11,401,306 B2

SEQUENCE LISTING, following Column 39 and 40, delete SEQUENCE ID NO 26 and replace with SEQUENCE ID NO 26 as follows:

```
<210> SEQ ID NO 26
<211> LENGTH: 18
<212> TYPE: PRT
<213> ORGANISM: Artificial Sequence
<220> FEATURE:
<223> OTHER INFORMATION: Synthetic

<400> SEQUENCE: 26

Lys Ser Ser Gly Gln Ala Glu Pro Asp Arg Ala His Tyr Asn Ile Val Thr Phe
1               5                   10                  15
```

SEQUENCE LISTING, following Column 39 and 40, delete SEQUENCE ID NO 27 and replace with SEQUENCE ID NO 27 as follows:

```
<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Lys Ser Ser Tyr Met Leu Asp Leu Gln Pro Glu Thr Thr
1               5                   10
```

SEQUENCE LISTING, following Column 39 and 40, delete SEQUENCE ID NO 28 and replace with SEQUENCE ID NO 28 as follows:

```
<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE 28

Lys Ser Ser Leu Leu Met Gly Thr Leu Gly Ile Val
1               5                   10
```